(12) United States Patent
Duan et al.

(10) Patent No.: US 9,696,316 B2
(45) Date of Patent: Jul. 4, 2017

(54) CONFORMATIONALLY DYNAMIC PEPTIDES

(71) Applicant: SYSTEM OF SYSTEMS ANALYTICS, INC., Fairfax, VA (US)

(72) Inventors: D. Roxanne Duan, Bethesda, MD (US); Jonathan R. Moll, Rockville, MD (US); Alan Rudolph, Potomac, MD (US); Renee Wegrzyn, Washington, DC (US)

(73) Assignee: SYSTEM OF SYSTEMS ANALYTICS, INC., Fairfax, VA (US)

( * ) Notice: Subject to any disclaimer, the term of this patent is extended or adjusted under 35 U.S.C. 154(b) by 29 days.

(21) Appl. No.: 14/299,432

(22) Filed: Jun. 9, 2014

(65) Prior Publication Data

US 2015/0133632 A1    May 14, 2015

Related U.S. Application Data

(63) Continuation of application No. 12/695,968, filed on Jan. 28, 2010, now abandoned.

(60) Provisional application No. 61/148,659, filed on Jan. 30, 2009.

(51) Int. Cl.
| | |
|---|---|
| *G01N 33/58* | (2006.01) |
| *C07K 14/47* | (2006.01) |
| *G01N 33/542* | (2006.01) |
| *G01N 33/68* | (2006.01) |
| *C07K 14/00* | (2006.01) |
| *C07K 19/00* | (2006.01) |

(52) U.S. Cl.
CPC ......... *G01N 33/582* (2013.01); *C07K 14/001* (2013.01); *C07K 14/4711* (2013.01); *C07K 19/00* (2013.01); *G01N 33/542* (2013.01); *G01N 33/6896* (2013.01)

(58) Field of Classification Search
None
See application file for complete search history.

(56) References Cited

U.S. PATENT DOCUMENTS

| | | | |
|---|---|---|---|
| 6,821,504 B2 | 11/2004 | Wisniewski et al. | |
| 7,166,471 B2 | 1/2007 | Orser et al. | |
| 7,282,373 B2 * | 10/2007 | Ebright | C07K 5/0821 435/69.7 |
| 7,691,639 B2 | 4/2010 | Orser et al. | |
| 8,062,895 B2 | 11/2011 | Orser et al. | |
| 8,372,593 B2 | 2/2013 | Orser et al. | |
| 8,673,579 B2 | 3/2014 | Orser et al. | |
| 2006/0057701 A1 | 3/2006 | Rosenthal et al. | |
| 2008/0095706 A1 * | 4/2008 | Orser | G01N 33/6896 424/9.1 |
| 2010/0233095 A1 | 9/2010 | Duan et al. | |

FOREIGN PATENT DOCUMENTS

WO    WO 2011/056958    *   5/2011

OTHER PUBLICATIONS

Ma et al. ('Stabilities and conformations of Alzheimer's beta-amyloid peptide oligomers (Abeta16-22, Abeta16-35, and Abeta10-35): sequence effects' PNAS v99(22) Oct. 29, 2002 pp. 14126-14131).*
Molgen Lectures (retrieved from http://lectures.molgen.mpg.de/ProteinStructure/Levels/ on Jun. 2, 2016, 4 pages).*
Donald et al. ('Salt Bridges: geometrically specific, designable interactions' Proteins v79 2011 pp. 898-915).*
Amino acids (retrieved from http://www.imgt.org/IMGTeducation/Aide-memoire/_UK/aminoacids/charge/ on Jun. 14, 2016, 3 pages).*
Abbvie Deutschland v. Janssen Biotech and Centorcor Biologics, App. No. 2013-1338, -1346 (Fed. Cir. , Jul. 1, 2014) total of 38 pages.*
Ghosh et al. ('Role of backbone hydration and salt-bridge formation in stability of alpha-helix in solution' Biophysical Journal v85 Nov. 2003 pp. 3187-3193).*
U.S. Appl. No. 14/445,846, filed Jul. 29, 2014, Wegrzyn et al.
U.S. Appl. No. 14/484,683, filed Sep. 12, 2014, Orser et al.
U.S. Appl. No. 14/299,432, filed Jun. 9, 2014, Duan et al.
U.S. Appl. No. 14/584,560, filed Dec. 29, 2014, Duan et al.
U.S. Appl. No. 14/296,721, filed Jun. 5, 2014, Feuerstein et al.
International Search Report issued on Jul. 27, 2010 in application No. PCT/US2010/022435.
Office Action issued on May 21, 2012 in U.S. Appl. No. 12/695,968 (US 2010/0233095).
Office Action issued on Dec. 5, 2012 in U.S. Appl. No. 12/695,968 (US 2010/0233095).
Office Action issued on May 15, 2013 in U.S. Appl. No. 12/695,968 (US 2010/0233095).
Office Action issued on Dec. 10, 2013 in U.S. Appl. No. 12/695,968 (US 2010/0233095).

* cited by examiner

*Primary Examiner* — Karlheinz R Skowronek
*Assistant Examiner* — Ronald Niebauer
(74) *Attorney, Agent, or Firm* — Foley & Lardner LLP

(57) ABSTRACT

Disclosed are novel peptides that are useful, for example, for detecting target proteins having a β-sheet secondary structure which may be associated with a disease, and for diagnosing and treating such a disease. Related methods and kits also are disclosed.

12 Claims, 18 Drawing Sheets

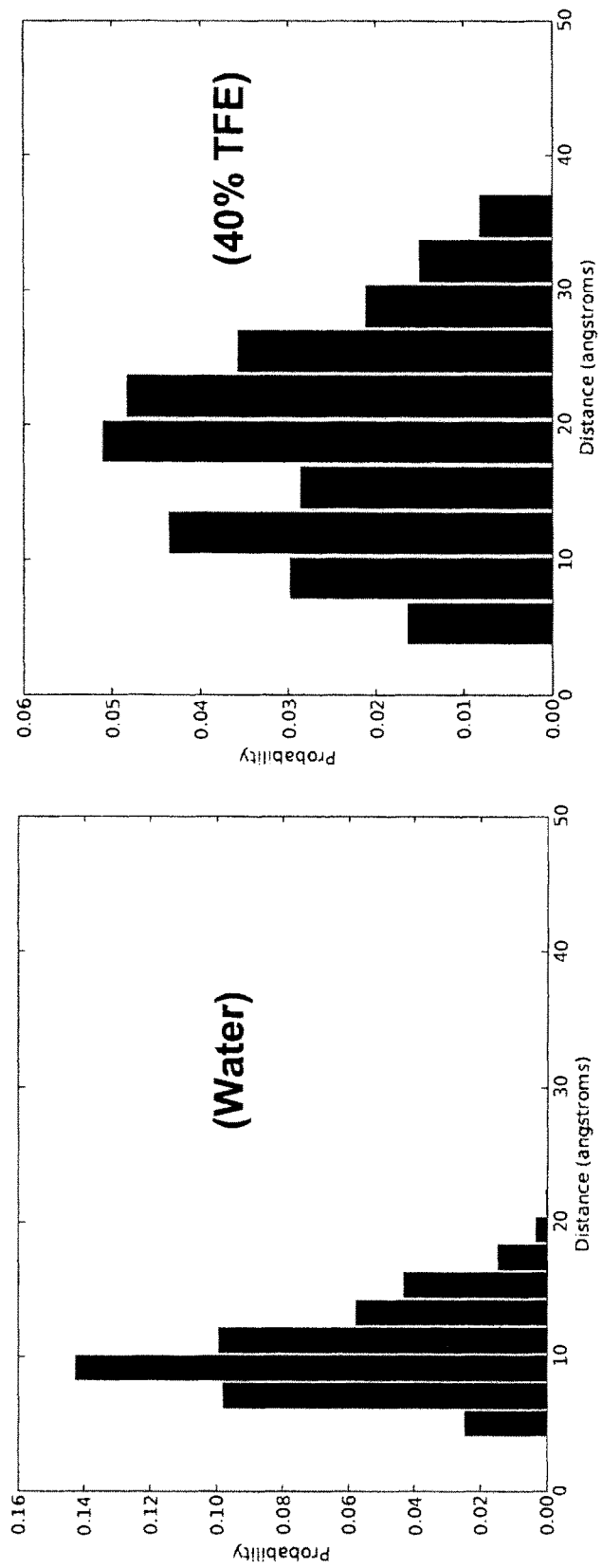

Figure 2

| | | | | | | | | | | | | | | | | | | | |
|---|---|---|---|---|---|---|---|---|---|---|---|---|---|---|---|---|---|---|---|
| WT (SEQ ID NO:1) | K | L | V | F | F | A | E | D | V | G | S | N | K | G | A | I | I | G | L | M | K |
| Peptide 22 (SEQ ID NO:2) | K | L | V | F | F | A | E | D | V | G | S | N | K | G | A | I | I | E | L | M | K |
| Peptide 38 (SEQ ID NO:3) | K | L | V | F | F | A | E | D | A | A | A | A | K | H | A | I | I | E | L | M | K |
| Peptide 45 (SEQ ID NO:4) | K | A | A | A | F | A | E | D | V | G | S | N | K | H | A | I | I | E | L | M | K |
| I32S (SEQ ID NO:5) | K | L | V | F | F | A | E | D | V | G | S | N | K | H | A | I | S | G | L | M | K |
| M35A (SEQ ID NO:6) | K | L | V | F | F | A | E | D | V | G | S | N | K | G | A | I | I | G | L | A | K |
| E22P (SEQ ID NO:7) | K | L | V | F | F | A | P | D | V | G | S | N | K | G | A | I | I | G | L | M | K |
| GM6 (SEQ ID NO:8) | K | L | V | S | F | A | E | D | V | G | S | N | K | G | A | I | I | G | P | M | K |
| A21G (SEQ ID NO:9) | K | L | V | F | F | G | E | D | V | G | S | N | K | G | A | I | I | G | L | M | K |
| E22G (SEQ ID NO:10) | K | L | V | F | F | A | G | D | V | G | S | N | K | G | A | I | I | G | L | M | K |
| E22Q (SEQ ID NO:11) | K | L | V | F | F | A | Q | D | V | G | S | N | K | G | A | I | I | G | L | M | K |
| E22K (SEQ ID NO:12) | K | L | V | F | F | A | K | D | V | G | S | N | K | G | A | I | I | G | L | M | K |
| D23N (SEQ ID NO:13) | K | L | V | F | F | A | E | N | V | G | S | N | K | G | A | I | I | G | L | M | K |

▒ indicates change to "wild type" Aβ sequence

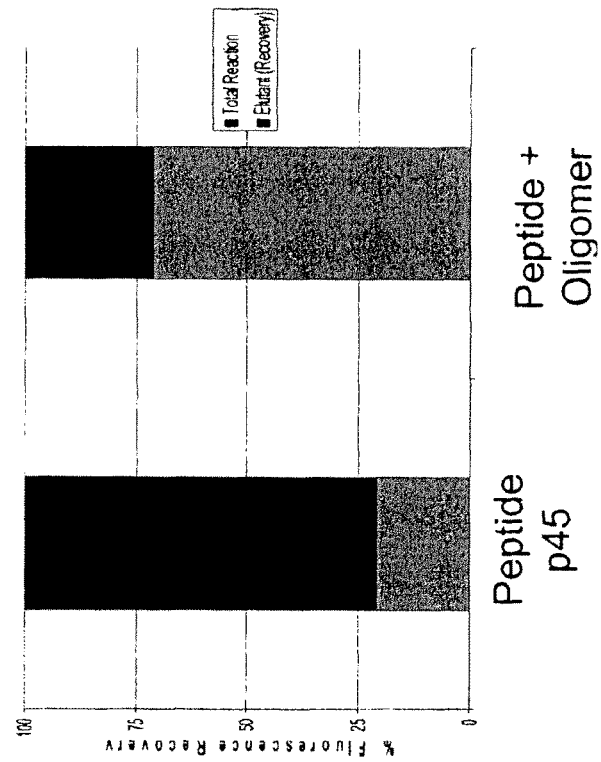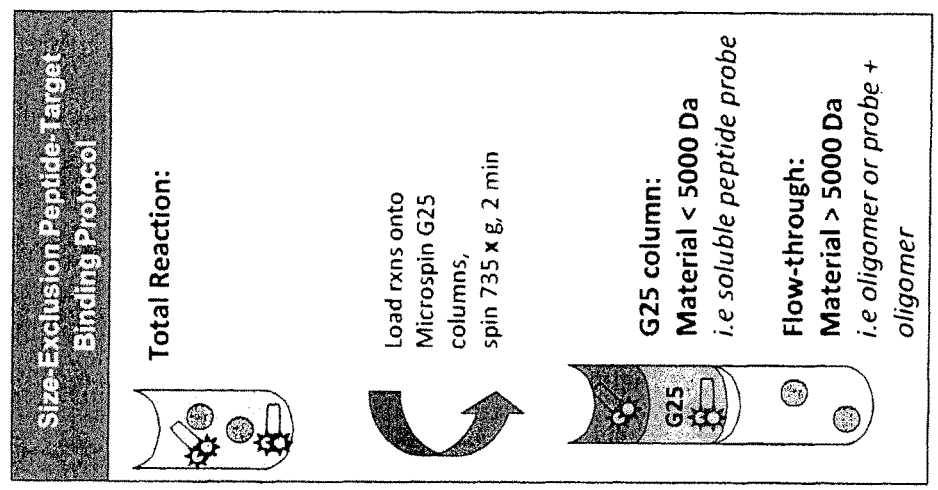
FIG. 4A
FIG. 4B

1. Aβ control (Input)
2. Beads+Oligo (Protocol A)
3. Beads+Oligo (Protocol B)
4. Peptide probe input
5. Beads+Oligo+p22 (Protocol A)
6. Beads+p22 (Protocol B)
7. Beads+Oligo+p22 (Protocol B)

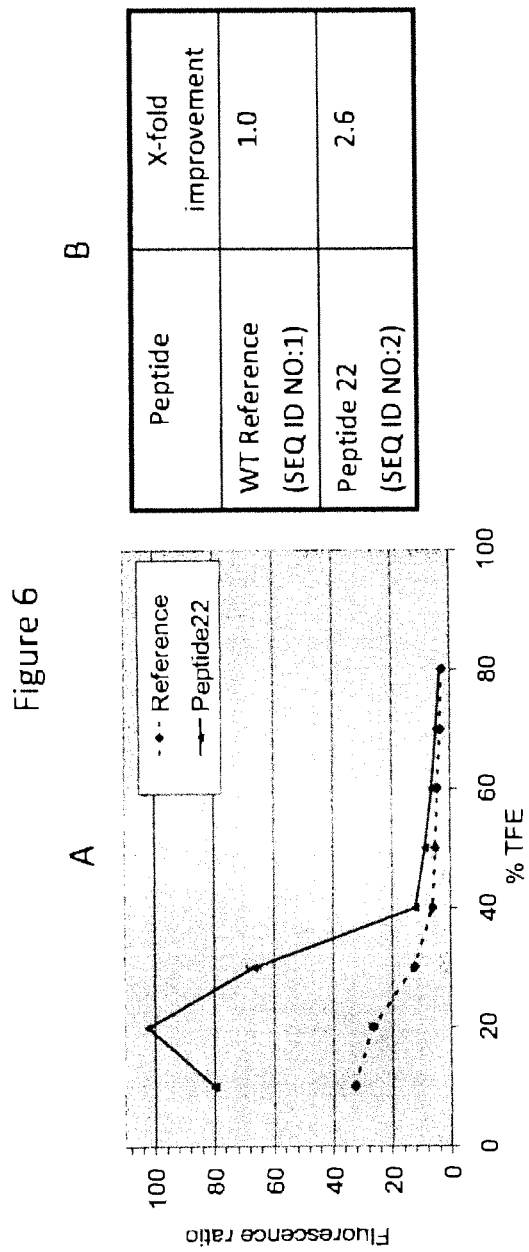

Figure 9
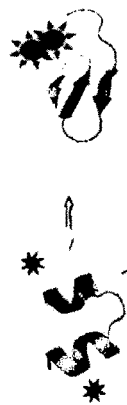
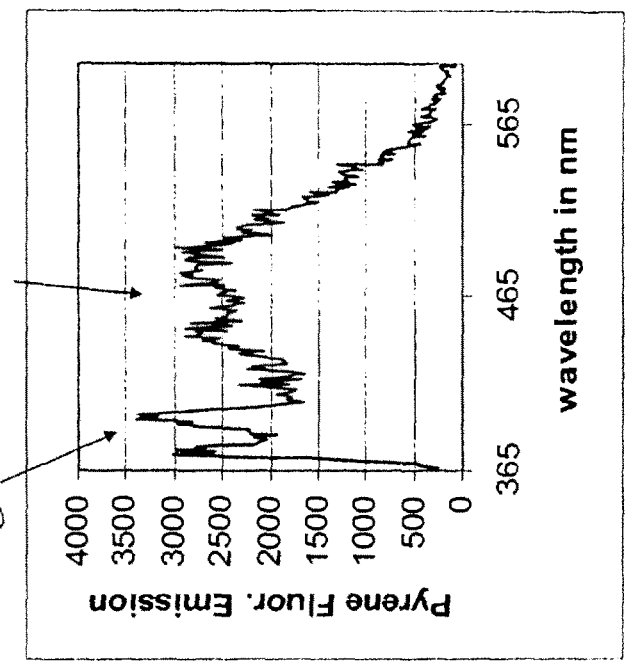
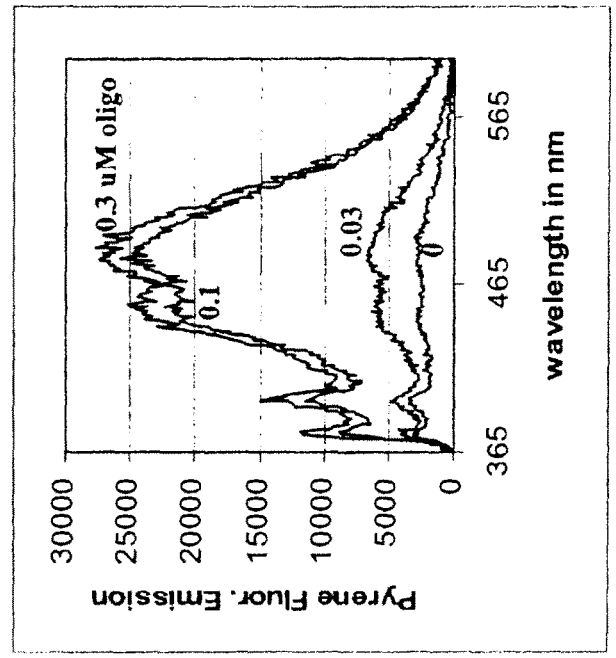

1. Aβ control (Input)
2. Beads+Oligo (Protocol A)
3. Beads+Oligo (Protocol B)
4. WT Probe input
5. Beads+Oligo+WT Probe (Protocol A)
6. Beads+WT Probe (Protocol B)
7. Beads+Oligo+WT Probe (Protocol B)

SEQUENCE LISTING

<160> NUMBER OF SEQ ID NOS: 60

<210> SEQ ID NO 1
<211> LENGTH: 21

```
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1

Lys Leu Val Phe Phe Ala Glu Asp Val Gly Ser Asn Lys Gly Ala Ile
1               5                   10                  15

Ile Gly Leu Met Lys
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 2

Lys Leu Val Phe Phe Ala Glu Asp Val Gly Ser Asn Lys His Ala Ile
1               5                   10                  15

Ile Glu Leu Met Lys
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 3

Lys Leu Val Phe Phe Ala Glu Asp Ala Ala Ala Ala Lys His Ala Ile
1               5                   10                  15

Ile Glu Leu Met Lys
            20

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 4

Lys Ala Ala Ala Lys Leu Val Phe Phe Ala Glu Asp Val Gly Ser Asn
1               5                   10                  15

Lys His Ala Ile Ile Glu Leu Met Lys
            20                  25

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 5

Lys Leu Val Phe Phe Ala Glu Asp Val Gly Ser Asn Lys Gly Ala Ile
1               5                   10                  15
```

Ser Gly Leu Met Lys
            20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 6

Lys Leu Val Phe Phe Ala Glu Asp Val Gly Ser Asn Lys Gly Ala Ile
1               5                   10                  15

Ile Gly Leu Ala Lys
            20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 7

Lys Leu Val Phe Phe Ala Pro Asp Val Gly Ser Asn Lys Gly Ala Ile
1               5                   10                  15

Ile Gly Leu Met Lys
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 8

Lys Leu Val Ser Phe Ala Glu Asp Val Gly Ser Asn Lys Gly Ala Ile
1               5                   10                  15

Ile Gly Pro Met Lys
            20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 9

Lys Leu Val Phe Phe Gly Glu Asp Val Gly Ser Asn Lys Gly Ala Ile
1               5                   10                  15

Ile Gly Leu Met Lys
            20

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

```
<400> SEQUENCE: 10

Lys Leu Val Phe Phe Ala Gly Asp Val Gly Ser Asn Lys Gly Ala Ile
1               5                   10                  15

Ile Gly Leu Met Lys
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 11

Lys Leu Val Phe Phe Ala Gln Asp Val Gly Ser Asn Lys Gly Ala Ile
1               5                   10                  15

Ile Gly Leu Met Lys
            20

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 12

Lys Leu Val Phe Phe Ala Lys Asp Val Gly Ser Asn Lys Gly Ala Ile
1               5                   10                  15

Ile Gly Leu Met Lys
            20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 13

Lys Leu Val Phe Phe Ala Glu Asn Val Gly Ser Asn Lys Gly Ala Ile
1               5                   10                  15

Ile Gly Leu Met Lys
            20

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 14

Lys Leu Val Phe Phe Ala Glu Asp Val Gly Ser Asn Lys Arg Ala Ile
1               5                   10                  15

Ile Glu Leu Met Lys
            20

<210> SEQ ID NO 15
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 15

Lys Leu Val Phe Phe Ala Glu Asp Val Gly Ser Asn Lys Lys Ala Ile
1               5                   10                  15

Ile Glu Leu Met Lys
            20

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 16

His His Gln Lys Leu Val Phe Phe Ala Glu Asp Glu Gly Ser Arg Lys
1               5                   10                  15

His Ala Ile Glu Gly Leu Met Glu Gly Lys
            20                  25

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 17

Glu Ala Ala Lys Leu Val Phe Phe Ala Glu Asp Glu Gly Ser Arg Lys
1               5                   10                  15

His Ala Ile Glu Gly Leu Met Glu Gly Lys
            20                  25

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 18

Lys Leu Val Phe Phe Ala Glu Asp Val Gly Ser Asn Lys Gly Ala Ile
1               5                   10                  15

Ser Gly Leu Met Lys
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 19

Lys Leu Val Phe Phe Ala Lys Asp Val Gly Ser Asn Lys His Ala Ile
1               5                   10                  15
```

```
Ile Glu Leu Met Lys
            20

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 20

Lys Leu Val Phe Phe Ala Gln Asp Val Gly Ser Asn Lys His Ala Ile
1               5                   10                  15

Ile Glu Leu Met Lys
            20

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 21

Lys Leu Val Phe Phe Ala Gly Asp Val Gly Ser Asn Lys His Ala Ile
1               5                   10                  15

Ile Glu Leu Met Lys
            20

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (22)..(23)
<223> OTHER INFORMATION: D-Arg

<400> SEQUENCE: 22

Lys Leu Val Phe Phe Ala Glu Asp Val Gly Ser Asn Lys Gly Ala Ile
1               5                   10                  15

Ile Gly Leu Met Lys Arg Arg
            20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (22)..(23)
<223> OTHER INFORMATION: D-Arg

<400> SEQUENCE: 23

Lys Leu Val Phe Phe Ala Glu Asp Val Gly Ser Asn Lys His Ala Ile
1               5                   10                  15

Ile Glu Leu Met Lys Arg Arg
            20
```

```
<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (1)..(2)
<223> OTHER INFORMATION: D-Arg

<400> SEQUENCE: 24

Arg Arg Lys Leu Val Phe Phe Ala Glu Asp Val Gly Ser Asn Lys His
1               5                   10                  15

Ala Ile Ile Glu Leu Met Lys Glu Glu
            20                  25

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (2)..(3)
<223> OTHER INFORMATION: Any amino acid

<400> SEQUENCE: 25

Gly Xaa Xaa Glu Gly
1               5

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (26)..(27)
<223> OTHER INFORMATION: D-Arg

<400> SEQUENCE: 26

Lys Ala Ala Ala Lys Leu Val Phe Phe Ala Glu Asp Val Gly Ser Asn
1               5                   10                  15

Lys His Ala Ile Ile Glu Leu Met Lys Arg Arg
            20                  25

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (26)..(27)
<223> OTHER INFORMATION: D-Arg

<400> SEQUENCE: 27

Lys Ala Ala Ala Lys Leu Val Phe Phe Ala Glu Asp Val Gly Ser Asn
1               5                   10                  15
```

```
Lys Gly Ala Ile Ile Gly Leu Met Lys Arg Arg
            20                  25

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 28

Lys Leu Val Phe Phe Ala Glu Asp Val Gly Ser Asn Lys Asp Ala Asp
1               5                   10                  15

Ile Glu Leu Met Lys
            20

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 29

Lys Leu Val Phe Phe Ala Glu Asp Val Gly Asp Asn Lys His Ala Ile
1               5                   10                  15

Ile Glu Leu Met Lys
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 30

Lys Leu Val Phe Phe Ala Glu Asp Val Gly Ser Asn Lys His Ala Asp
1               5                   10                  15

Ile Glu Leu Met Lys
            20

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 31

Lys Leu Val Phe Phe Ala Glu Asp Val Gly Ser Asn Lys His Ala Ile
1               5                   10                  15

Ile Glu Asp Met Lys
            20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      probe
```

```
<400> SEQUENCE: 32

Lys Leu Val Phe Phe Ala Glu Asp Val Gly Ser Asn Lys Asp Ala Ile
1               5                   10                  15

Ile Glu Leu Met Lys
            20

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 33

Lys Leu Val Phe Phe Ala Glu Asp Val Gly Asp Asn Lys His Ala Asp
1               5                   10                  15

Ile Glu Leu Met Lys
            20

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 34

Lys Leu Val Ser Phe Ala Glu Asp Val Gly Ser Asn Lys His Ala Ile
1               5                   10                  15

Ile Glu Pro Met Lys
            20

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 35

Lys Leu Val Ser Phe Ala Glu Asp Val Gly Ser Asn Lys His Ala Ile
1               5                   10                  15

Ile Glu Leu Met Lys
            20

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 36

Lys Leu Val Phe Phe Ala Glu Asp Val Gly Ser Asn Lys Gly Ala Ile
1               5                   10                  15

Ile Gly Leu Met Lys
            20

<210> SEQ ID NO 37
```

```
<211> LENGTH: 25
<212> TYPE: PRT
<213> ORGANISM: Artificial Sequence
<220> FEATURE:
<223> OTHER INFORMATION: Description of Artificial Sequence: Synthetic
      probe
<220> FEATURE:
<221> NAME/KEY: MOD_RES
<222> LOCATION: (23)..(25)
<223> OTHER INFORMATION: D-Arg

<400> SEQUENCE: 37

Glu Lys Leu Val Phe Phe Ala Glu Asp Val Gly Ser Asn Lys Gly Ala
1               5                   10                  15

Ile Ile Gly Leu Met Lys Arg Arg Arg
            20                  25

<210> SEQ ID NO 38
<211> LENGTH: 26
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 38

Lys Leu Val Phe Phe Ala Glu Asp Val Gly Ser Asn Lys His Ala Ile
1               5                   10                  15

Ile Glu Leu Met Lys Glu Ala Ala Ala Lys
            20                  25

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 39

Lys Leu Val Phe Phe Ala Glu Asp Val Gly Ser Asn Lys His Ala Ile
1               5                   10                  15

Ile Glu Leu Met Lys
            20

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 40

Lys Leu Val Phe Phe Ala Glu Asp Val Gly Ser Asn Lys His Ala Ile
1               5                   10                  15

Ile Glu Leu Met Lys Gly Ser Ser Gly Ser Ser Lys
            20                  25

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      probe
```

```
<400> SEQUENCE: 41

Lys Leu Val Phe Phe Ala Glu Asp Val Gly Ser Asn Lys His Ala Ile
1               5                   10                  15

Ile Glu Leu Met Lys Gly Leu Val Pro Arg Gly Ser Gly Lys
            20                  25                  30

<210> SEQ ID NO 42
<211> LENGTH: 27
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 42

Lys Leu Val Phe Phe Ala Glu Asp Val Gly Ser Asn Lys His Ala Ile
1               5                   10                  15

Ile Glu Leu Met Lys Pro Ser Gly Ser Pro Lys
            20                  25

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 43

Lys Leu Val Phe Phe Ala Glu Asp Val Gly Ser Asn Lys His Ala Ile
1               5                   10                  15

Ile Glu Leu Met Lys
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 44

Glu Leu Val Phe Phe Ala Glu Asp Val Gly Ser Asn Lys Gly Ala Ile
1               5                   10                  15

Ile Gly Leu Met Lys
            20

<210> SEQ ID NO 45
<211> LENGTH: 40
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 45

Glu Arg His Asp Ser Gly Tyr Glu Val His His Gln Lys Leu Val Phe
1               5                   10                  15

Phe Ala Glu Asp Val Gly Ser Asn Lys Gly Ala Ile Ile Gly Leu Met
            20                  25                  30

Val Gly Gly Val Val Ile Ala Lys
        35                  40
```

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence: Synthetic probe

<400> SEQUENCE: 46

Glu Glu Phe Arg His Asp Ser Gly Tyr Glu Val His His Gln Lys Leu
1               5                   10                  15

Val Phe Phe Ala Glu Asp Val Gly Ser Asn Lys Gly Ala Ile Ile Gly
            20                  25                  30

Leu Met Lys
        35

<210> SEQ ID NO 47
<211> LENGTH: 27
<212> TYPE: PRT
<213> ORGANISM: Artificial Sequence
<220> FEATURE:
<223> OTHER INFORMATION: Description of Artificial Sequence: Synthetic probe

<400> SEQUENCE: 47

Glu Ala Ala Ala Lys Leu Val Phe Phe Ala Glu Asp Glu Gly Ser Arg
1               5                   10                  15

Lys His Ala Ile Glu Gly Leu Met Glu Gly Lys
            20                  25

<210> SEQ ID NO 48
<211> LENGTH: 27
<212> TYPE: PRT
<213> ORGANISM: Artificial Sequence
<220> FEATURE:
<223> OTHER INFORMATION: Description of Artificial Sequence: Synthetic probe

<400> SEQUENCE: 48

Glu His His Gln Lys Leu Val Phe Phe Ala Glu Asp Glu Gly Ser Arg
1               5                   10                  15

Lys His Ala Ile Glu Gly Leu Met Glu Gly Lys
            20                  25

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic probe

<400> SEQUENCE: 49

Glu Leu Val Phe Phe Ala Glu Asp Val Gly Ser Asn Lys His Ala Ile
1               5                   10                  15

Ile Glu Leu Met Lys
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic probe

```
<400> SEQUENCE: 50

Lys Leu Val Phe Phe Ala Glu Asp Val Gly Ser Asn Lys His Ala Ile
1               5                   10                  15

Ile Glu Leu Met Trp
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 51

Lys Leu Val Phe Phe Ala Glu Asp Val Gly Ser Asn Lys Gly Ala Ile
1               5                   10                  15

Ile Gly Leu Met Glu
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 52

Lys Leu Val Phe Phe Ala Glu Asp Val Gly Ser Asn Lys His Ala Ile
1               5                   10                  15

Ile Glu Leu Met Glu
            20

<210> SEQ ID NO 53
<211> LENGTH: 34
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 53

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Glu

<210> SEQ ID NO 54
<211> LENGTH: 26
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 54

His His Gln Lys Leu Val Phe Phe Ala Glu Asp Glu Gly Ser Arg Lys
1               5                   10                  15

His Ala Ile Glu Gly Leu Met Glu Gly Glu
            20                  25
```

<210> SEQ ID NO 55
<211> LENGTH: 26
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 55

Glu Ala Ala Lys Leu Val Phe Phe Ala Glu Asp Glu Gly Ser Arg Lys
1               5                   10                  15

His Ala Ile Glu Gly Leu Met Glu Gly Glu
            20                  25

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Ala Ala Ala Lys
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Ser Ser Gly Ser Ser Lys
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Val Pro Arg Gly Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Leu Val Pro Arg Gly Ser Gly Lys
1               5

<210> SEQ ID NO 60
<211> LENGTH: 6
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 60

Pro Ser Gly Ser Pro Lys
1               5
```

CONFORMATIONALLY DYNAMIC PEPTIDES

CROSS-REFERENCE TO RELATED APPLICATION

This application claims the benefit under 35 U.S.C. §119 (e) of U.S. Provisional Patent Application No. 61/148,659, filed Jan. 30, 2009, and is a continuation application of U.S. application Ser. No. 12/695,968, filed Jan. 28, 2010. The contents of these applications are which is incorporated herein by reference in their entirety.

BACKGROUND

1. Field of the Invention

The present invention provides conformationally dynamic peptides that are useful, for example, for detecting target proteins having a specific conformation, including misfolded proteins or proteins having a β-sheet secondary structure which may be associated with a disease. Also provided are methods of detecting such target proteins, diagnosing diseases associated with such target proteins or risk thereof, and treating diseases associated with such target proteins.

2. Background

The pathogenesis of misfolded protein disorders is characterized by the conversion of normal proteins into aggregation-prone β-sheet rich conformations. In the case of Alzheimer's disease (AD), self-assembly of amyloid beta (Aβ) protein into neurotoxic oligomers and fibrils is well supported as causative of disease. Other misfolded proteins associated with disease include prions in transmissible spongiform encephalopathy (TSE), cerebral amyloid angiopathy (CAA), and cerebral vascular disease (CVD); α-synuclein deposits in Lewy bodies of Parkinson's disease, tau in neurofibrillary tangles in frontal temporal dementia and Pick's disease; superoxide dismutase in amylotrophic lateral sclerosis; and Huntingtin in Huntington's disease. See, e.g., Glenner et al., *J. Neurol. Sci.* 94:1-28, 1989; Haan et al., *Clin. Neurol. Neurosurg.* 92(4):305-310, 1990.

U.S. Pat. No. 7,166,471, US 2006/0286672, US 2005/0026165, US 2008/0171341, US 2006/0057671 and US 2008/0095706 describe peptides useful for the detection of, for example, misfolded proteins, target protein having a predominantly β-sheet secondary structure, and target protein in a specific state of self-aggregation. The peptides described herein can be used in the methods described in any of these patent documents, the contents of each of which are incorporated herein by reference in their entirety.

SUMMARY OF THE INVENTION

In accordance with some embodiments, there is provided peptide probes for a target protein capable of exhibiting a β-sheet conformation associated with an amyloidogenic disease, wherein the peptide probe (i) consists of from 10 to 50 amino acid residues comprising an amino acid sequence that is a variant of a reference sequence consisting of an amino acid sequence of a β-sheet forming region of the target protein, (ii) is capable of adopting both a random coil/alpha-helix conformation and a β-sheet conformation, and (iii) adopts a β-sheet conformation upon binding to target protein exhibiting a β-sheet conformation or undergoes a change in conformation that generates a detectable signal upon binding to target protein. The variant sequence comprises one or more amino acid additions, substitutions or deletions relative to the reference sequence, such that (A) the random coil/alpha-helix conformation of the variant sequence is more stable in an oxidizing environment than a probe consisting of the reference amino acid sequence and/or (B) the distance between the N-terminus and the C-terminus of the variant sequence in a random coil/alpha-helix conformation differs from the distance between the N-terminus and the C-terminus of the variant sequence in a β-sheet conformation and/or (C) the variant sequence adopts a β-sheet conformation upon binding to target protein exhibiting a β-sheet conformation more efficiently than the reference sequence and/or (D) the variant sequence adopts a less ordered conformation upon binding to target protein exhibiting a β-sheet conformation and/or (E) the β-sheet structure of the variant sequence is less thermodynamically strong than that of the reference sequence and/or (F) the variant sequence has increased stability and/or decreased reactivity than the reference sequence and/or (G) the variant sequence has an increased hydrophilicity and/or solubility in aqueous solutions than the reference sequence and/or (H) the variant sequence has an additional Aβ binding motif than the reference sequence and/or (I) the variant sequence has an enhanced ability to form aggregates. In some embodiments, the variant sequence further comprises the addition of a lysine residue at the C-terminus.

In some embodiments, the peptide probe is labeled with a detectable label, such as a fluorescent label, at the N-terminus, the C-terminus, both termini, or at one or more positions that generate a signal when the peptide adopts a β-sheet conformation or undergoes a conformation change upon binding to target protein. In some embodiments, the peptide probe is labeled with two or more labels, wherein the distance between two or more labels on the peptide probe when the peptide probe is bound to target protein is different than the distance when the peptide probe is not bound to target protein. In some embodiments, the signal generated by the detectable label when the peptide probe is bound to target protein is different than the signal generated when the peptide probe is not bound to target protein, such such as the signal when the peptide probe exhibits a β-sheet conformation being greater than the signal generated when the peptide probe exhibits a random coil/alpha-helix conformation. In any of these embodiments, the peptide probe may be labeled with a detectable label pair selected from an excimer pair, a FRET pair and a fluorophore/quencher pair. When the peptide probe is labeled with an excimer pair, such as a pyrene pair, it may emit an excimer signal when the peptide probe exhibits a β-sheet conformation. When the peptide probe is labeled with a FRET pair, such as DACIA-I/NBD, Marina Blue/NBD, Dansyl/Trp, and EDANS/FAM, it may emit a fluorescence resonance transfer (FRET) signal when the peptide probe exhibits a β-sheet conformation. When the peptide probe is labeled with a fluorophore/quencher pair, such as pyrene/Dabcyl, EDANS/Dabcyl and FAM/Dabcyl, the fluorphore signal may be quenched when the peptide probe exhibits a β-sheet conformation.

In some embodiments, the one or more amino acid additions, substitutions or deletions in the peptide probe are made at an internal portion of the reference sequence, or are made at the N-terminus or C-terminus of the reference sequence, or at both termini, or internally and terminally.

In some embodiments, the variant sequence comprises the substitution of a methionine residue with a residue resistant to oxidation, such as an alanine residue. In some embodiments, the variant sequence comprises the substitution of at least three consecutive residues of the reference sequence with alanine residues.

Additionally or alternatively, in some embodiments, the one or more amino acid additions, substitutions or deletions introduces a salt bridge between two residues, such as between a glutamic acid residue and a histidine residue, a glutamic acid residue and an arginine residue, and/or a glutamic acid residue and a lysine residue.

Additionally or alternatively, in some embodiments, the one or more amino acid additions, substitutions or deletions introduces an Aβ binding motif into the peptide probe, such as a GXXEG motif (SEQ ID NO:25).

Additionally or alternatively, in some embodiments, the variant sequence adopts a less ordered conformation upon binding to target protein exhibiting a β-sheet conformation. In specific embodiments, the target protein is Aβ protein, and the variant sequence comprises one or more substitutions selected from the group consisting of G29H, G29R, G29K, and G33E. Additionally or alternatively, the β-sheet structure of the variant sequence may be less thermodynamically strong than that of the reference sequence. In specific embodiments, the variant sequence comprises one or more substitutions selected from the group consisting of I32S, F19S, S26D, H29D, I31D, L34D, and L34P.

Additionally or alternatively, in some embodiments, the variant sequence has an increased hydrophilicity and/or solubility in aqueous solutions than the reference sequence. In specific embodiments, the variant sequence comprises one or more amino acid additions or substutions that introduce a glutamic acid residue and/or a d-arginine residue. Additionally or alternatively, the variant sequence may be conjugated to a hydrophilic moiety, such as a soluble polyethylene glycol moiety.

In accordance with any of the foregoing embodiments, a detectable label may be conjugated to a side chain of a terminal lysine residue of the peptide probe, and/or to a side chain of an internal lysine residue of the peptide probe.

In accordance with any of the foregoing embodiments, the peptide probe may be conjugated to a biotin moiety, such as through a peptide linker. In specific embodiments, the peptide linker is selected from the group consisting of a flexible linker, a helical linker, a thrombin site linker and a kinked linker. In more specific embodiments, the linker comprises an amino acid sequence selected from the group consisting of SEQ ID NO:56-60. In other embodiments, the peptide probe is conjugated to a biotin moiety through a side chain of an internal lysine residue.

In accordance with some embodiments, the peptide probe is a peptide or peptide mimic that (i) consists of from 10 to 50 amino acid residues comprising an amino acid sequence that is a variant of a reference sequence consisting of an amino acid sequence of a β-sheet forming region of the target protein, (ii) is capable of adopting both a random coil/alpha-helix conformation and a β-sheet conformation, and (iii) adopts a less ordered conformation upon binding to target protein. In further embodiments, such a peptid probe is labeled with a detectable label at the N-terminus, the C-terminus, both termini, or at one or more positions that generate a signal when the peptide undergoes a conformation change upon binding to target protein, such as being labeled with a detectable label pair selected from an excimer pair, a FRET pair and a fluorophore/quencher pair. In specific embodiments, the peptide probe is labeled with an excimer pair (such as two pyrene moieties) and emits an increased excimer signal when the peptide probe is not bound to target protein and emits an increased self signal when the peptide probe is bound to target protein. In other specific embodiments, the peptide probe is labeled with a FRET pair and emits an increased a fluorescence resonance transfer (FRET) signal when the peptide probe is not bound to target protein and emits a non-FRET fluorophore signal when the peptide probe is bound to target protein. In other specific embodiments, the peptide probe is labeled with a fluorophore/quencher pair and emits a decreased or quenched signal when the peptide probe is not bound to target protein and emits a fluorophore signal when the peptide probe is bound to target protein. In accordance with any embodiments described herein, the variant sequence may comprise or consist of an amino acid sequence selected from the group consisting of SEQ ID NOs: 2-55. In specific embodiments, the variant sequence comprises or consists of the amino acid sequence of SEQ ID NO:2 (Peptide 22).

In some embodiments, the variant sequence comprises the substitution of at least one residue with a glutamic acid residue. In some embodiments, the variant sequence comprises the substitution of at least one residue with a histidine residue. In some embodiments, the variant sequence comprises one or more substitutions selected from the group consisting of an isoleucine residue with a serine residue; glutamic acid residue with either a proline residue, a glycine residue, a glutamine residue or a lysine residue; a phenylalanine residue with a serine residue; a leucine residue with a proline residue; an alanine residue with a glycine residue; and an aspartic acid residue with an asparagine residue. In some embodiments, the variant sequence comprises the addition of a lysine residue at the C-terminus. In some embodiments, the peptide probe comprises an amino acid sequence selected from the group consisting of SEQ ID NOs:2-8.

In accordance with other embodiments, there is provided method for detecting target protein in a test sample, wherein the target protein exhibits a β-sheet conformation associated with an amyloidogenic disease, comprising (i) contacting the sample with any peptide probe described herein to form a test mixture; and (ii) detecting any binding between the peptide probe and any target protein present.

In some embodiments, step (ii) comprises detecting any signal generated by the fluorescent label of peptide probe exhibiting a β-sheet conformation or undergoing a conformational change upon binding to a target protein. In some embodiments, step (ii) comprises detecting complexes comprising the peptide probe and target protein by detecting any signal generated by any detectable label (such as a fluorescent label) present in the complexes. In some embodiments, the complexes are insoluble complexes (such as amyloid beta fibrils) and step (ii) comprises detecting any signal generated by any detectable label (such as a fluorescent label) present in the insoluble complexes. In some embodiments, the complexes are soluble complexes (such as amyloid beta oligomers) and step (ii) comprises detecting any signal generated by any detectable label (such as a fluorescent label) present in the soluble complexes. In some embodiments, the method further comprises, prior to step (ii), separating the complexes from the test mixture by a process comprising centrifugation, size exclusion chromatography, or affinity chromatography.

In accordance with other embodiments, there is provided a method for detecting target protein associated with an amyloidogenic disease, wherein the peptide probe in a physiological sample from a subject, comprising (A) contacting the sample with a peptide probe that is a peptide or peptide mimic that (i) consists of from 10 to 50 amino acid residues comprising an amino acid sequence that is a variant of a reference sequence consisting of an amino acid sequence of a β-sheet forming region of the target protein, (ii) is capable of adopting both a random coil/alpha-helix conformation and a β-sheet conformation, and (iii) adopts a less ordered conformation upon binding to target protein; and (B) detecting any association between said probe and any target protein present in the sample. In some embodiments, the peptide probe is labeled with a detectable label at the N-terminus, the C-terminus, both termini, or at one or more positions that generate a signal when the peptide undergoes a conformation change upon binding to target protein. In specific embodiments, the peptide probe is labeled with an excimer pair and step (ii) comprises detecting any increased self signal or decreased excimer signal. In other embodiments, the peptide probe is labeled with a FRET pair and step (ii) comprises detecting any increased non-FRET fluorophore signal or decreased FRET signal. In other embodiments, the peptide probe is labeled with a fluorophore/quencher pair and step (ii) comprises detecting any increased fluorophore signal.

In other embodiments, there is provided an in vivo method for detecting target protein associated with an amyloidogenic disease in subject, comprising (A) administering to the subject any peptide probe as described herein, wherein the probe is labeled with a detectable label that generates a signal when the probe binds to target protein and (B) detecting the signal. In some embodiments, the signal is detected using an imaging technique, such as positron emission tomography (PET), single photon emission computed tomography (SPECT), magnetic resonance imaging (MRI), radiography, tomography, fluoroscopy, nuclear medicine, optical imaging, encephalography and ultrasonography.

In other embodiments, there is provided a method of treating a subject suffering from or at risk of developing an amyloidogenic disease, comprising administering to the subject any peptide probe described herein. In some embodiments, the probe is conjugated to an additional therapeutic agent against said amyloidogenic disease.

In accordance with any embodiments described herein, the target protein may selected from the group consisting of amyloid islet polypeptide precursor protein, amyloid beta protein, Aβ peptide, serum amyloid A, insulin, amylin, non-amyloid beta component, prions, hemoglobin, immunoglobulins or fragments thereof β2-microglobulin, α-synuclein, rhodopsin, α1-antichymotrypsin, cystallins, tau, p53, presenilins, low-density lipoprotein receptor, apolipoproteins, superoxide dismutase, neurofilament proteins, transthyretin, procalcitonin or calcitonin, atrial natriuretic factor, gelsolin, cystic fibrosis transmembrane regulator, Huntington's disease protein, fibrinogen alpha-chain, phenylalanine hydroxylase, collagen, beta-hexosaminidase, and cystatin C protein. In accordance with specific embodiments, the target protein may be Aβ protein.

BRIEF DESCRIPTION OF THE DRAWINGS

FIG. 1A illustrates the in silico predictions for the distribution of inter-pyrene distances of pyrenes conjugated to each terminus of a peptide corresponding to a region of the Aβ peptide, depending on the solvent environment of the pyrenated peptide (left panel:water, right panel; 40% TFE).

FIG. 2 sets forth specific embodiments of peptides described herein (SEQ ID NOs 2-13) and their amino acid additions and/or substitutions relative to a wildtype reference sequence (SEQ ID NO:1), which is based on amino acids 16-35 of the "wild-type" Aβ protein with an added lysine at the C terminus for conjugating to a fluorescent label.

FIGS. 4A and 4B illustrate an in vitro size exclusion chromatography-based interaction assay using a labeled peptide probe (SEQ ID NO:4) to detect soluble Aβ42 target protein oligomers, with results illustrated in FIG. 4B, which shows that the fluorescently labeled peptide is recovered in the presence of the oligomer, indicating that the peptide probe binds the target protein oligolmers. Similar results were obtained with a labeled peptide probe of SEQ ID NO:1, as shown in FIG. 14.

FIG. 6A illustrates the determination of the maximal signal gain associated with a solvent-induced conformational change of a peptide described herein (Peptide 22; SEQ ID NO:2) as compared to a reference peptide (SEQ ID NO:1). FIG. 6B reports the results of a determination of the maximal signal gain associated with a conformational change of the peptide in the presence of fibrillar amyloid target protein, as compared to that of the reference peptide.

FIGS. 9A and B illustrate the effect of the interaction of Aβ42 oligomer (target protein) on the pyrene fluorescence properties of Peptide 45 (SEQ ID NO:4). FIG. 9A shows the fluorescence emission of the peptide-target complex. FIG. 9B shows the fluorescence emission of the peptide alone.

The fluorescence of Peptide 22 is stable over time in the absence of oligomer (no increase in monomer or excimer flourescence), but exhibits an increase in pyrene monomer signal when incubated with soluble Aβ oligomers. (solid line=Time 0; dashed line=3 hours; dotted line=18 hours).

Figure 12:
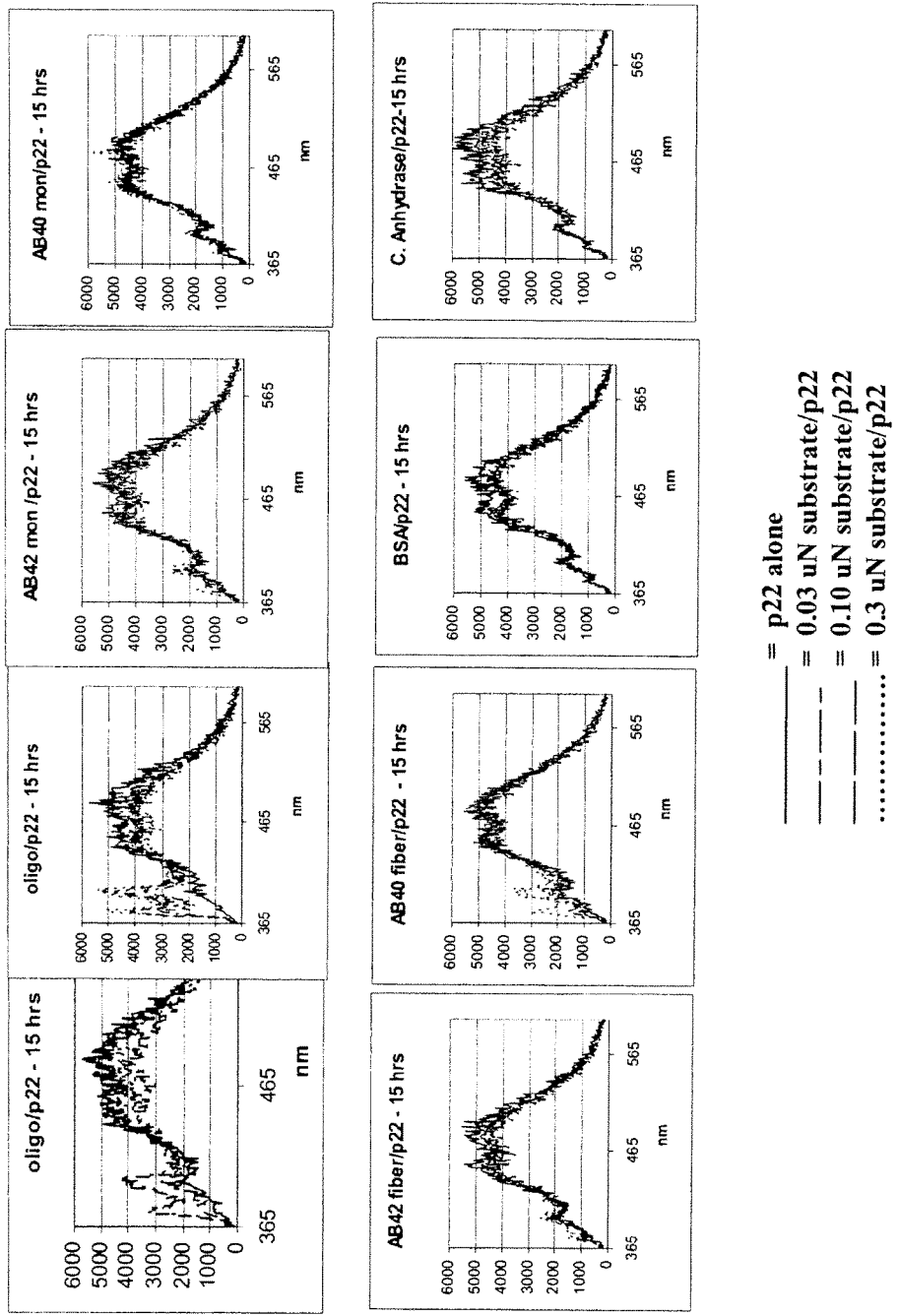

FIG. 12 illustrates the specificity of Peptide 22 (SEQ ID NO:2) for soluble Aβ oligomers. The first two panels show the dose-dependent increase in pyrene monomer signal when Peptide 22 is incubated with soluble Aβ oligomers prepared by two different methods. The next two panels show no change in fluorescence when Peptide 22 is incubated with Aβ40 monomers and Aβ42 monomers. The next panel shows no change in fluorescence when Peptide 22 is incubated with Aβ40 fibers and the next panel shows some dose-dependent increase in monomer fluorescence when Peptide 22 is incubated with Aβ42 fibers. The last two panels show no change in fluorescence when Peptide 22 is incubated with control solutions (BSA or Anhydrase). The data show the natural log (Ln) of the monomer fluorescence area over time. (dotted line=0.3 uM substrate; dashed line=0.1 uM; dashed/dot line=0.03 uM; solid line=p22 alone).

FIGS. 13A and B illustrate the conformation change of Peptide 22 (SEQ ID NO:2) upon interaction with soluble Aβ42 oligomers. FIG. 13A shows the change in fluorescence of Peptide 22 upon interaction with soluble Aβ42 oligomer, with a shift from excimer to monomer fluorescence. (solid line—no Aβ42 oligomer; dashed/dot line—30 nN Aβ42 oligomer; large dashed line—100 nN Aβ42 oligomer; small dashed line—300 nN Aβ42 oligomer) FIG. 13B shows the secondary structure of Peptide 22 as determined by CD analysis, which does not detect a conformation change in the presence of Aβ42 oligomer that is detectable by the change in pyrene fluorescence. (solid line—Peptide 22; dashed/dot line—Aβ42 oligomer; large dashed line—arithmetic sum of results of individual samples; small dashed line—mixture of Peptide 22 and Aβ42 oligomer)

Figure 14B:
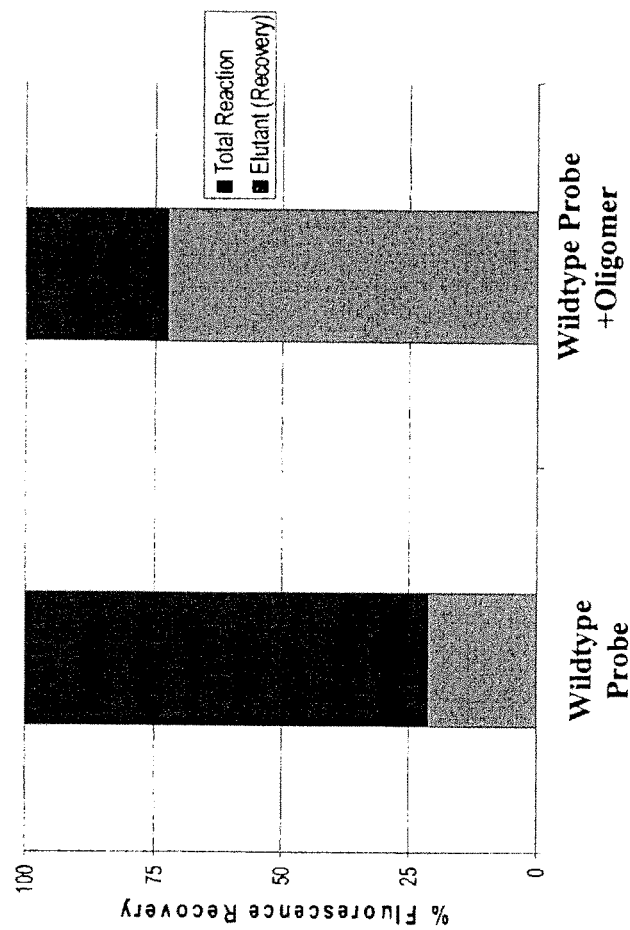
Figure 14A:
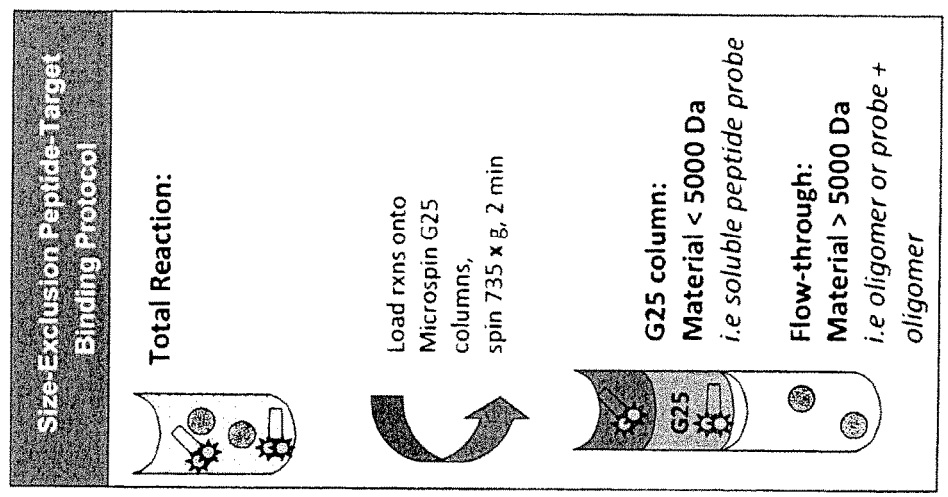

FIGS. 14A and 14B illustrate an in vitro size exclusion chromatography-based interaction assay using a labeled peptide probe (SEQ ID NO:1) to detect soluble Aβ42 target protein oligomers, with results illustrated in FIG. 14B, which shows that the fluorescently labeled peptide is recovered in the presence of the oligomer, indicating that the peptide probe binds the target protein oligolmers.

Figure 15B:
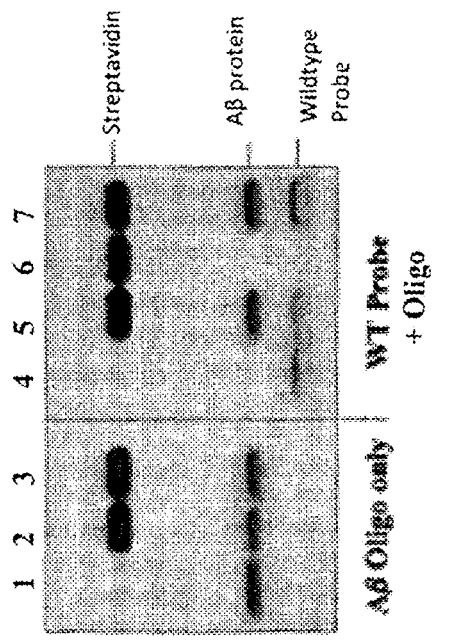
Figure 15A:
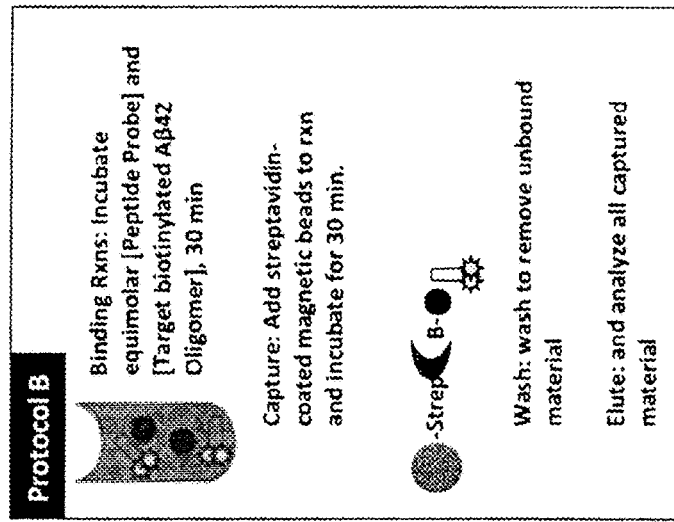

FIGS. 15A and 15B illustrate an in vitro affinity chromatography-based interaction assay using a labeled peptide probe (SEQ ID NO: 1) to detect biotin-labeled soluble Aβ42 target protein oligomers, with results illustrated in FIG. 15B, which shows that labeled peptide probe is only detected in the captured material, in the presence of high molecular weight oligomers, indicating that the peptide probe binds the target protein oligolmers.

DETAILED DESCRIPTION

1. Definitions

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein "subject" denotes any animal in need of detection or therapeutic treatment, including humans and domesticated animals, such as cats, dogs, swine, cattle, sheep, goats, horses, rabbits, and the like. "Subject" also includes animals used in research settings, including mice and other small mammals. A typical subject may be at risk of a condition, disease or disorder or suspected of suffering from such a condition, or may be desirous of determining risk or status with respect to a particular condition, such as a condition, disease or disorder associated with a target protein. As used herein, "therapeutic" treatment includes the administration of a therapeutic agent to treat an existing condition, to prevent a condition that the subject is at risk or developing, or for health maintenance.

As used herein, "conformation" refers to particular secondary structure of a protein or peptide, for example, an alpha-helix, random coil or β-sheet secondary structure. A "conformational change" is a change from one conformation to another.

"Prion" refers to proteins associated with prion-based diseases. "PrP protein", "PrP", and the like are used interchangeably herein to mean both the infections particle form ("PrP$^{Sc}$") known to cause diseases (such as spongiform encephalopathies) in humans and animals, and the non-infectious form ("PrP$^C$") which, under appropriate conditions, is converted to the infectious PrP$^{Sc}$ form. Prion particles are comprised largely, if not exclusively, of PrP$^{Sc}$ molecules encoded by a PrP gene. As used herein, "prion" includes all forms of prions causing all or any of these diseases or others in any animals used, and in particular in humans and domesticated farm animals.

As described herein, "amyloidogenic diseases" are diseases in which amyloid plaques or amyloid deposits are formed in the body. Amyloid formation is found in a number of disorders, such as diabetes, AD, scrapie, BSE, CJD, chronic wasting disease (CWD), related transmissible spongiform encephalopathies (TSEs), and other diseases disclosed herein. The invention is not limited to amyloidogenic diseases, however, and is useful in the diagnosis and treatment of any disease or condition associated with a specific conformation or aggregative state of a protein.

The term "Aβ protein" is used herein to refer to all forms of the Aβ protein, including $AB_{40}$ and $AB_{42}$. "Aβ" protein also includes all naturally occurring mutants, including naturally occurring mutants known to exhibit increased tendency to form aggregates. Such mutants are known in the art, such as those disclosed in Murakami et al., *J. Biol. Chem.* 46:46179-46187, 2003, which is incorporated herein by reference in its entirety.

"Target protein" is used herein to refer to any protein suitable for targeting, detection of identification by the present invention, such as those proteins capable of a conformational change. Target proteins may be associated with a disease state characterized by a β-sheet conformation as described herein. Target proteins may be naturally occurring proteins.

"Native" or "naturally occurring" proteins refer to proteins recovered from a source occurring in nature. A native protein would include post-translational modifications, including, but not limited to, acetylation, carboxylation, glycosylation, phosphorylation, lipidation, acylation, and cleavage. "Protein," "peptide" and "polypeptide" are used interchangeably.

"Peptide mimic" is also referred to as a peptidomimic or peptidomimetic and refers to any molecule that mimics the properties of a peptide. Peptide mimics include polymeric molecules that mimic the folding and/or secondary structure of a specific peptide, as well as those that mimic the biological or chemical properties of a peptide. Peptide mimics may have an amino acid backbone and contain non-natural chemical or amino acid substitutions. Alternatively, peptide mimics may have different chemical backbones, such as (3-peptides, anthranilamide oligomers, oligo (m-phenylene ethynylene), oligourea, oligopynolinones, azatides and N-substituted glycine oligomers. Peptide mimics may have different chemical properties, such as resistance to proteases, while retaining peptide characteristics, such as peptide folding and peptide-peptide interactions (including, for example, interactions via hydrogen bonding, etc.). Any suitable peptide mimic can be used in the present invention, and include those designed and/or constructed as described in Chongsiriwatana, N. P, et al. *Proc Natl Acad Sci USA* 2008, 105, (8), 2794-9; Kirshenbaum, K., et al. *Current Opinion in Structural Biology* 1999, 9, (4), 530-535; Lee, B. c., et al., *Journal of the American Chemical Society* 2005, 127, (31), 10999-11009, which are each hereby incorporated by reference in their entirety.

"Similarity" between two polypeptides is determined by comparing the amino acid sequence of one polypeptide to the sequence of a second polypeptide. An amino acid of one polypeptide is similar to the corresponding amino acid of a second polypeptide if it is identical or a conservative amino acid substitution. Conservative substitutions include those described in Dayhoff, M. O., ed., *The Atlas of Protein Sequence and Structure* 5, National Biomedical Research Foundation, Washington, D.C. (1978), and in Argos, P. (1989) *EMBO J.* 8:779-785. For example, amino acids belonging to one of the following groups represent conservative changes or substitutions:

Ala, Pro, Gly, Gln, Asn, Ser, Thr:
Cys, Ser, Tyr, Thr;
Val, Ile, Leu, Met, Ala, Phe;
Lys, Arg, His;
Phe, Tyr, Trp, His; and
Asp, Glu.

"Homology", "homologs of", "homologous", "identity", or "similarity" refers to sequence similarity between two polypeptides, with identity being a more strict comparison. Homology and identity may each be determined by comparing a position in each sequence that may be aligned for purposes of comparison. When a position in the compared sequence is occupied by the same amino acid, then the molecules are identical at that position. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares 10% or less identity, with one of the sequences described herein. Related sequences share more than 10% sequence identity, such as at least about 15% sequence identity, at least about 20% sequence identity, at least about 30% sequence identity, at least about 40% sequence identity, at least about 50% sequence identity, at least about 60% sequence identity, at least about 70% sequence identity, at least about 80% sequence identity, at least about 90% sequence identity, at least about 95% sequence identity, or at least about 99% sequence identity.

The term "percent identity" refers to sequence identity between two amino acid sequences. Identity may be determined by comparing a position in each sequence that is aligned for purposes of comparison. When an equivalent position in one compared sequences is occupied by the same amino acid in the other at the same position, then the molecules are identical at that position; when the equivalent site occupied by the same or a similar amino acid residue (e.g., similar in stearic and/or electronic nature), then the molecules may be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as part of the GCG sequence analysis package (University of Wisconsin, Madison, Wis.), and may be used with, e.g., default settings. ENTREZ is available through the National Center for Biotechnology Information, National Library of Medicine, NIH, Bethesda, Md.). In one embodiment, the percent identity of two sequences may be determined by the GCG program with a gap weight of 1, e.g., each amino acid gap is weighted as if it were a single amino acid mismatch between the two sequences. Other techniques for determining sequence identity are well known and described in the art.

2. Target Proteins and Diseases

Proteins that are associated with human or animal disease when they adopt a specific conformational or self-aggregated state are known in the art. Examples of such diseases includes amyloidogenic diseases, including Alzheimer's disease (AD), cerebral amyloid angiopathy (CAA), and cerebral vascular disease (CVD). As used herein, "amyloidogenic diseases" are diseases in which amyloid plaques or amyloid deposits are formed in the body. Amyloid formation is found in a number of disorders, such as diabetes, AD, scrapie, bovine spongiform encephalopathy (BSE), Creutzfeldt-Jakob disease (CJD), chronic wasting disease (CWD), related transmissible spongiform encephalopathies (TSEs).

A variety of diseases are associated with a specific structural form of a protein (e.g., a "misfolded protein" or a self-aggregated protein), while the protein in a different structural form (e.g., a "normal protein") is not harmful. Thus, for these conditions, a β-sheet conformation could be a target structural state for detection of the disease, while an alpha-helix and/or random coil conformation could be a target structural state to confirm absence of the disease, or to identify absence of an advanced state of the disease. In many cases, the normal protein is soluble, while the misfolded protein forms insoluble aggregates.

The following is a non-limiting list of diseases associated with specific structural protein states, followed parenthetically by the involved protein: Alzheimer's Disease (APP, Aβ peptide, α1-antichymotrypsin, tau, non-Aβ component, presenilin 1, presenilin 2, apoE); prion diseases, CJD, scrapie, and BSE (PrPSc); ALS (SOD and neurofilament); Pick's disease (Pick body); Parkinson's disease (α-synuclein in Lewy bodies); frontotemporal dementia (tau in fibrils); diabetes type II (amylin); multiple myeloma-plasma cell dyscrasias (IgGL-chain); familial amyloidotic polyneuropathy (transthyretin); medullary carcinoma of thyroid (procalcitonin); chronic renal failure (β2-microglobulin); congestive heart failure (atrial natriuretic factor); senile cardiac and systemic amyloidosis (transthyretin); chronic inflammation (serum amyloid A); atherosclerosis (ApoA1); familial amyloidosis (gelsolin); and Huntington's disease (Huntingtin). Also, prions in transmissible spongiform encephalopathy (TSE); cerebral amyloid angiopathy (CAA), and cerebral vascular disease (CVD); and superoxide dismutase in amylotrophic lateral sclerosis. See, e.g., Glenner et al., *J. Neurol. Sci.* 94:1-28, 1989; Haan et al., *Clin. Neural. Neurosurg.* 92(4):305-310, 1990.

Often, these insoluble proteins form aggregates composed of non-branching fibrils with the common characteristic of a β-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions. See, e.g., Mandybur, *Acta Neuropathol.* 78:329-331, 1989; Kawai et al., *Brain Res.* 623:142-146, 1993; Martin et al., *Am. J. Pathol.* 145:1348-1381, 1994; Kalaria et al., *Neuroreport* 6:477-80, 1995; Masliah et al., *J. Neurosci.* 16:5795-5811, 1996. Other studies additionally indicate that amyloid fibrils may actually initiate neurodegeneration. See, e.g., Lendon et al., *J. Am. Med. Assoc.* 277:825-831, 1997; Yankner, *Nat. Med.* 2:850-852, 1996; Selkoe, *J. Biol. Chem.* 271:18295-18298, 1996; Hardy, *Trends Neurosci.* 20:154-159, 1997.

While the underlying molecular mechanism that results in protein misfolding is not well understood, a common characteristic for all the above mentioned neurological disorders is the formation of fibrils which come together to form a β-sheet structure. Fibril formation and the subsequent formation of secondary β-sheet structures associated with plaque deposits, occurs via a complex mechanism involving a nucleation stage, in which monomers of the protein associate to form fibrils, followed by extension of the fibrils at each end. Thus, peptide, protein or antibody probes that are capable of disrupting fibril formation would prevent disease progression and thus be of therapeutic importance. Additionally, agents capable of associating with a particular self-associating state of the diseased protein are useful diagnostic tools to detect and quantify a particular form of the misfolded protein, as well as provide insights to the progression of the disease. Thus, highly selective peptide agents capable of associating with specific proteins in a particular state of self-aggregation are useful, both as detection agents as well as for therapeutic applications.

The present invention provides peptide probes and methods for detecting misfolded target protein associated with diseases. Such misfolded proteins may exhibit and increase in β-sheet secondary structure or conformation and may form insoluble aggregates, fibrils or deposits such as plaques that are hallmarks of such diseases.

(i) Amyloidogenic Diseases

Amyloid beta protein (Aβ) is the primary causative agent in amyloiodogenic diseases such as Alzheimer's disease (AD), cerebral amyloid angiopathy (CAA), and cerebral vascular disease (CVD). Soluble Aβ is found in the plasma and cerebrospinal fluid of healthy individuals, and disease appears to correlate with insoluble fibrils forming plaques or aggregates found in diseased individuals.

Aβ is generated by cleaving the amyloid beta precursor protein (APP) at any of several sites, resulting in several forms of Aβ. Two abundant forms found in amyloid plaques are $A\beta_{1-40}$ (also referred to as Aβ40) and $A\beta_{1-42}$ (also referred to as Aβ42), which are produced by alternative carboxy-terminal truncation of APP. See, e.g., Selkoe et al., PNAS USA 85:7341-7345, 1988; Selkoe, *Trends Neurosci.* 16:403-409, 1993. Aβ40 and Aβ42 have identical amino acid sequences, with Aβ42 having two additional residues (Ile and Ala) and its C terminus. Although Aβ40 is more abundant, Aβ42 is the more fibrillogenic and is the major component of the two in amyloid deposits of both AD and CAA. See, e.g., Wurth et al., J. Mol. Biol. 319: 1279-90 (2002). As noted above, all naturally occurring mutants of Aβ protein can be a target protein or serve as the basis of a reference sequence in the context of the present invention.

Elevated plasma levels of Aβ42 have been associated with AD, and with increased risk for AD. Also, the magnitude of the ratio of Aβ42/Aβ40 levels has been shown to have clinical significance for AD, CAA, and other conditions, such as late-life depression (LLMD). See, e.g., Pomara et al. Neurochem. Res. (2006). Plasma levels of Aβ42 and Aβ40 are typically determined using monoclonal antibodies. In addition to the amyloid deposits in AD cases described above, most AD cases are also associated with amyloid deposition in the vascular walls. See, e.g., Vinters H. V., Stroke March-April; 18(2):311-324, 1987; Itoh Y., et al., Neurosci. Lett. 155(2):144-147, Jun. 11, 1993.

(ii) Prion Diseases and Transmissible Spongiform Encephalopathies

Prions are infections pathogens that cause central nervous system spongiform encephalopathies in humans and animals. A potential prion precursor is a protein referred to as PrP 27-30, a 28 kilodalton hydrophobic glycoprotein that polymerizes (aggregates) into rod-like filaments found as plaques in infected brains. The normal prion protein ($PrP^C$) is a cell-surface metallo-glycoprotein that has mostly an α-helix and coiled-loop structure. The abnormal form ($PrP^{Sc}$) is a conformer that is resistant to proteases and has a secondary structure that contains predominantly n-sheets. It is believed that this conformational change in secondary structure leads to aggregation and eventual neurotoxic plaque deposition in the prion disease process.

Prion-associated diseases, also known as Transmissible Spongiform Encephalopathies or "TSEs," include scrapie of sheep and goats, chronic wasting disease of deer and elk, and bovine spongiform encephalopathy (BSE) of cattle. See, e.g., Wilesmith and Wells, *Microbial. Immunol.* 172:21-38, 1991. Four prion diseases of humans have been identified: (1) kuru, (2) Creutzfeldt-Jakob disease (CJD), (3) Gerstmann-Strassler-Scheinker Disease (GSS), and (4) fatal familial insomnia (FFI). See, e.g., Gajdusek, D. C., *Science* 197:943-969, 1977; Medori et al. *N. Engl. J. Med.* 326:444-449, 1992. TSEs are fatal neurodegenerative disease. These diseases are characterized by the formation and accumulation in the brain of an abnormal proteinase K resistant isoform (PrP-res) of a normal protease-sensitive, host-encoded prion protein (PrP-sen). PrP-res is formed from PrP-sen by a post-translational process involving conformational changes that convert the PrP-sen into a PrP-res molecular aggregate having a higher β-sheet content. The formation of these macromolecular aggregates of PrP-res is closely associated with TSE-mediated brain pathology, in which amyloid deposits of PrP-res are formed in the brain, which eventually becomes "spongiform" (filled with holes).

The cellular protein PrP-sen is a sialoglycoprotein encoded by a gene that, in humans, is located on chromosome 20. The PrP gene is expressed in both neural and non-neural tissues, with the highest concentration of its mRNA being found in neurons. Sequences of Prp genes are disclosed in U.S. Pat. No. 5,565,186, which is incorporated herein by reference.

3. Conformationally Dynamic Peptides

Described herein are conformationally dynamic peptides that are useful, for example, for detecting target proteins having a specific conformation, including misfolded proteins or proteins having a β-sheet secondary structure which may be associated with a disease. The peptides also are useful in methods of diagnosing diseases associated with such target proteins or risk thereof, and treating diseases associated with such target proteins.

The peptides are useful as probes for a target protein capable of exhibiting or exhibiting a β-sheet conformation associated with an amyloidogenic disease. The peptides are capable of adopting both a random coil/alpha-helix conformation and a β-sheet conformation. In some embodiments, the peptides adopt a β-sheet conformation upon binding to target protein exhibiting a β-sheet conformation. In other embodiments, the peptides adopt a less ordered (e.g., decreased β-sheet) conformation upon binding to target protein exhibiting a β-sheet conformation.

Peptide probes comprising amino acid residues 16-35 of the Aβ protein sequence (SEQ ID NO:1) have been described previously. Such probes contain the hydrophobic core responsible for both intramolecular β-sheet formation and protein aggregation. While this "wildtype" peptide performs as expected in fiber-based assays in organic solvents (e.g., it has an alpha helical structure in 40% TFE in the absence of substrate, and undergoes a transition to a β-sheet structure upon introduction of Aβ fibril substrate), other properties make it less than ideal for use in in vitro assays. For example, it has a low solubility in aqueous solutions, and its β-sheet structure is thermodynamically strong and resistant to conformational change. Thus, peptide probes have been designed with more desirable properties to improve performance in in vitro assays and in vivo applications.

As described in more detail herein, in some embodiments the peptide probes have a variant sequence that comprises one or more amino acid additions, substitutions or deletions relative to the reference sequence, such that (A) the random coil/alpha-helix conformation of the variant sequence is more stable in an oxidizing environment than a probe consisting of the reference amino acid sequence and/or (B) the distance between the N-terminus and the C-terminus of the variant sequence in a random coil/alpha-helix conformation differs from the distance between the N-terminus and the C-terminus of the variant sequence in a β-sheet conformation and/or (C) the variant sequence adopts a β-sheet conformation upon binding to target protein exhibiting a β-sheet conformation more efficiently than the reference sequence.

Additionally or alternatively (particularly with reference to embodiment (C) above), the peptide probes may have a variant sequence that comprises one or more amino acid additions, substitutions or deletions relative to the reference sequence, such that (D) the variant sequence adopts a less ordered or decreased β-sheet conformation upon binding to target protein exhibiting a β-sheet conformation. In some more particular embodiments, (E) the β-sheet structure of the variant sequence is less thermodynamically strong than that of a probe consisting of the reference sequence.

Additionally or alternatively, the peptide probes have a variant sequence that comprises one or more amino acid additions, substitutions or deletions relative to the reference sequence, such that (F) the variant sequence has increased stability and/or decreased reactivity than a probe consisting of the reference sequence; (G) the variant sequence has an increased hydrophilicity and/or solubility in aqueous solutions than a probe consisting of the reference sequence and/or (H) the variant sequence has an additional Aβ binding motif than a probe consisting of the reference sequence.

Additionally or alternatively, the variant sequences comprise one or more amino acid additions, substitutions or deletions relative to the reference sequence such that (I) the variant sequence has an enhanced ability to form aggregates. In more particular aspects, the variant sequence may comprise a truncated form of a naturally occurring mutant.

Also described are methods and kits for using and screening the peptides.

In accordance with some embodiments, the peptides bind to the target protein in a conformation-dependent manner and undergo a structural conversion from predominantly random coil (unstructured) or alpha-helix conformations to β-sheet rich conformations, such as upon binding to a target protein exhibiting a β-sheet conformation. In these embodiments, the peptides generally change from a less ordered to a more ordered conformation. Conjugation of reporter moieties to these peptides can provide a simple mechanism for monitoring the conformational conversion (such as via a change in the fluorescent spectrum using fluorescently labeled peptides).

In accordance with other embodiments, the peptides bind to the target protein in a conformation-dependent manner and undergo a structural conversion from predominantly β-sheet rich conformations to a less ordered or decreased β-sheet conformations, or increased random coil (unstructured) or alpha-helix conformations, upon binding to a target protein exhibiting a β-sheet conformation. In these embodiments, the peptides generally change from a more ordered to a less ordered conformation. Conjugation of reporter moieties to these peptides can provide a simple mechanism for monitoring the conformational conversion (such as via a change in the fluorescent spectrum using fluorescently labeled peptides).

In accordance with some embodiments, the peptides are designed (such as, for example, by the selection of specific amino acid deletions, substitutions or additions) to improve their performance in different assay conditions (such as for use in an aqueous versus organic solvent, under different pH and/or salt conditions, etc).

Before particular embodiments of the invention are described and disclosed, it is to be understood that the particular materials, methods and compositions described herein are presented only by way of examples, and are not limiting of the scope of the invention. The technical and scientific terms used herein have the meanings commonly understood by one of ordinary skill in the art to which the present invention pertains, unless otherwise defined. Publications and other materials setting forth known methodologies to which reference is made are incorporated herein by reference in their entireties as though set forth in full.

The peptides described herein can be made by any method, such as direct synthesis or recombinantly. Standard reference works setting forth the general principles of recombinant DNA technology include Sambrook, J., et al. (1989) Molecular Cloning: A Laboratory Manual, 2d Ed., Cold Spring Harbor Laboratory Press, Planview, N.Y.; McPherson, M. J. Ed. (1991) Directed Mutagenesis: A Practical Approach, IRL Press, Oxford; Jones, J. (1992) Amino Acid and Peptide Synthesis, Oxford Science Publications, Oxford; Austen, B. M. and Westwood, O. M. R. (1991) Protein Targeting and Secretion, IRL Press, Oxford.

Any suitable materials and/or methods known to those of ordinary skill in the art can be utilized in carrying out the present invention. However, exemplary materials and methods are described. Materials, reagents and the like to which reference is made in the following description and examples are obtainable from commercial sources, unless otherwise noted.

As noted above, the conformationally dynamic peptides described herein are useful, for example, for detecting target proteins having a specific conformation, including misfolded proteins or proteins having a β-sheet secondary structure which may be associated with disease. For example, the peptides are useful as probes for a target protein capable of exhibiting or exhibiting a β-sheet conformation associated with an amyloidogenic disease. The peptides also may be useful in diagnostic and therapeutic approaches, and in methods of screening drug candidates. For convenience, the peptides are referred to herein as "probes" without detracting from their utility in other contexts.

In some embodiments, the peptide probe comprises an amino acid sequence that is a variant of a reference sequence, where the reference sequence consists of an amino acid sequence of the target protein that undergoes a conformational shift, such as a shift from an α-helix/random coil conformation to a β-sheet conformation. Such a region is referred to herein as "a β-sheet forming region" of the target protein. For example, amino acids 16-35 of the Aβ protein are known to comprises a β-sheet forming region. Thus, the reference sequence may comprise amino acids 16-35, or 17-35, of the Aβ protein. The amino acid sequence of the peptide may be designed, therefore, from the target protein sequence, based on existing sequence and conformation information or, alternatively, may be readily determined experimentally. In some embodiments, the reference sequence consists of an amino acid sequence of a β-sheet forming region of a naturally occurring mutant of the target protein, such as a mutant known to exhibit an increased tendency to adopt a β-sheet conformation and/or to form aggregates. Examples of Aβ mutants are described in Murakami, supra, and include the substitutions A21G, E22G, E22Q, E22K, and D23N.

The reference sequence may comprise a minimum number of contiguous amino acids of the target protein, such as at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 contiguous amino acids of the target protein sequence, or any range between these numbers, such as about 10 to about 25 contiguous amino acids of the target protein sequence.

The peptide probes themselves comprise at least about 5 amino acids, and may include up to about 300 to about 400 amino acids, or more, or any size in between, such as about 10 amino acids to about 50 amino acids in length. In some embodiments, the peptides consist of about 5 to about 100, about 10 to about 50, about 10 to about 25, about 15 to about 25, or about 20 to about 25 amino acids. In further embodiments, the peptides comprise from about 17 to about 34 amino acids, including about 20 amino acids, about 21 amino acids, about 22 amino acids, about 23 amino acids, about 24 amino acids, or about 25 amino acids. Peptides of different lengths may exhibit different degrees of interaction and binding to target protein, and suitable lengths can be selected by the skilled artisan guided by the teachings herein.

In some embodiments, the peptides undergo a structural change similar to that of the target protein. For example, in some embodiments, the peptides are capable of adopting both a random coil/alpha-helix conformation and a β-sheet conformation, and adopt a β-sheet conformation upon binding to target protein exhibiting a β-sheet conformation. In other embodiments the peptide probe is provided in a β-sheet conformation, and undergoes a conformational change to a less ordered or decreased β-sheet conformation/increased alpha-helix conformation upon contact, binding and/or interaction with target protein in a β-sheet conformation.

The peptides may be provided in a solution, such as an aqueous solution with a pH of between about 4 and about 10, such as between about 5 and about 8, with an ionic strength of between about 0.05 and about 0.5 (when typically prepared with a chloride salt, such as sodium chloride or potassium chloride). The solution may also comprise a water-miscible organic material, such as trifluoroethanol, in amounts between about 30% to about 70% by volume, such as between about 45% to about 60%. The solvent may be prepared with a suitable buffering system such as acetate/acetic acid, Tris, or phosphate.

As discussed in more detail below, the peptides probes disclosed herein may be used to detect target protein in vitro or in vivo. The peptide probes also are useful for identifying therapeutic agents, such as in accordance with the methods described in US 2008/0095706 (corresponding to U.S. patent application Ser. No. 11/828,953), the entire contents of which are incorporated herein by reference in their entireties.

(i) Variant Sequences

As noted above, in some embodiments, the peptide probe comprises an amino acid sequence that is a variant of a reference sequence that comprises one or more amino acid additions, substitutions or deletions relative to the reference sequence. In some embodiments the peptide consists of the variant sequence. As noted above, the reference sequence consists of an amino acid sequence of a β-sheet forming region of the target protein. In some embodiments, the variant sequence is designed to improve the performance of the peptide in assays for detecting target protein. For example, in some embodiments the variant is designed such that the random coil/alpha-helix conformation of the variant sequence is more stable in an oxidizing environment than a probe consisting of the reference amino acid sequence. Additionally or alternatively, the variant sequence is designed such that the distance between the N-terminus and the C-terminus of the variant sequence in a random coil/alpha-helix conformation differs from (e.g., is greater than) the distance between the N-terminus and the C-terminus of the variant sequence in a β-sheet conformation. Additionally or alternatively, the variant sequence is designed such that the variant sequence adopts a β-sheet conformation upon binding to target protein exhibiting a β-sheet conformation more efficiently than the reference sequence. Additionally or alternatively, the variant sequence is designed such that the variant sequence adopts a less ordered or decreased β-sheet conformation upon binding to target protein exhibiting a β-sheet conformation, and may have a β-sheet structure that is less thermodynamically strong than that of the reference sequence. Additionally or alternatively, the variant sequence may be designed such that the variant sequence has increased stability and/or decreased reactivity, increased hydrophilicity and/or solubility, and/or an additional Aβ binding motif. Additionally or alternatively, the variant sequence may comprise one or more amino acid deletions relative to the reference sequence, such that the variant sequence has an enhanced ability to form aggregates.

In some embodiments, the variant sequence is designed to increase the signal difference between any signal associated with peptide that is not bound to target protein and a signal associated with peptide that is bound to target protein, such as by increasing the signal difference between any signal associated with the random/alpha-helix conformation of the peptide (e.g., background signal) and a signal associated with the β-sheet conformation of the peptide. This may be effected by, for example, reducing any background signal associated with the random/alpha-helix conformation of the peptide and/or increasing a signal associated with the β-sheet conformation of the peptide. These same design rationales also are useful for peptide probes that are provided in a β-sheet conformation and adopt a less ordered or decreased β-sheet conformation/increased alpha-helix conformation upon binding to target protein, although the background signal would be associated with the probe's β-sheet conformation.

For example, the peptide probe may be labeled at or near each of its N- and C-termini, such that a signal is generated by interaction between the label moieties that occurs when the moieties are in physical proximity to each other, such as when the peptide exhibits a β-sheet conformation that brings the N- and C-termini into physical proximity. Such a signal would be associated with the β-sheet conformation of the peptide. Similarly, the peptide may be labeled at any one or more sites that is/are in physical proximity when the peptide is in a β-sheet conformation and distant when the peptide is in a random coil/α-helix configuration, such that the labels interact to emit a signal when the peptide is in the β-sheet conformation. A signal associated with the β-sheet conformation may be different from any signal associated with the random coil/alpha-helix conformation, such as by having a greater magnitude and/or being at a different frequency or wavelength.

In embodiments where the peptide probe changes from a less ordered to a more ordered conformation upon binding with target protein, background signal maybe observed, for example, if the random coil/alpha-helix conformation permits the labels to come into sufficient physical proximity to generate a signal and/or if the peptide probe adopts a β-sheet conformation that is not associated with contact, binding to or interaction with target protein, such as may occur in solution. Background signal associated with the random coil/alpha-helix conformation of the peptide could be reduced, for example, by stabilizing the random coil/alpha-helix conformation to minimize the formation of β-sheet conformation that is not associated with contact, binding to or interaction with target protein. For example, the peptide probe may be designed such that the random coil/alpha-helix conformation of unbound peptide probe exhibits increased stability. For example, substitutions with alpha-helix forming residues (such as alanine) and/or salt bridge forming residues (such as histidine and glutamic acid) may stabilize the random coil/alpha-helix conformation of unbound peptide probe. Such increased stability decreases the background signal by reducing the likelihood that the labels will be in sufficient physical proximity to generate a signal. Thus, in some embodiments, the variant sequence of the peptide comprises amino acid substitutions, additions and/or deletions that increase the stability of the random coil/alpha-helix conformation.

Additionally or alternatively, increasing the distance between the N- and C-termini (or between the sites of the labels) when the peptide is in a random coil/alpha-helix conformation would decrease any signal associated with the random/alpha-helix conformation. Additionally or alternatively, the signal associated with the β-sheet conformation of the peptide could be increased, for example, by decreasing the distance between the N- and C-termini (or between the sites of the labels) when the peptide is in a β-sheet conformation. Distances between the termini of the peptide (or between the label sites) in the random coil/alpha-helix conformation versus in the β-sheet conformation can be modeled in silico using standard protein modeling methods.

In the discussion below, point mutations are numbered based on the amino acid sequence of Aβ protein, residues 16-35 of which are set forth in FIG. 2 (with an added C-terminal lysine residue).

Alpha Helix Formation and Stability

In some embodiments, the variant sequence comprises the addition of, or substitution with, one or more amino acid residues that have a propensity for forming alpha helices, such as alanine (A). Such amino acid residues may be introduced into an internal site of the reference sequence, or at either or both termini of the reference sequence. In some embodiments, the reference sequence includes one, two, three, four, five, six, seven, eight, nine, ten, or more of such amino acid residues, as additional residues or in place of residues of the target protein (substitutions). In specific embodiments where the target protein is the Aβ protein, the peptide probe comprises the variant sequence of SEQ ID NO:3 (Peptide 38) or SEQ ID NO:4 (Peptide 45). In specific embodiments, the peptide probe consists of SEQ ID NO:3 or SEQ ID NO:4.

Introducing point mutations with complementary charged residues also may increase the propensity to form alpha helices, such as the mutations G29H and G33E in Aβ peptide probes. These particular substitutions also increase hydrophilicity and solubility in aqueous solutions. Thus, in specific embodiments where the target protein is the Aβ protein, the peptide probe comprises the variant sequence of SEQ ID NO:2 (Peptide 22), or consists of SEQ ID NO:2.

In other embodiments, any of the other variants described herein may be further modified to include alanine residues or complementary charged residues to enhance alpha helix formation.

Salt Bridges

In some embodiments, the variant sequence comprises one or more amino acid substitutions or additions that introduce amino acids capable of forming salt bridges or that introduce an amino acid capable of forming a salt bridge with an amino acid already present in the reference sequence. Salt bridges are weak ionic interactions between negatively and positively charged amino acids. In some embodiments, the amino acid substitutions or additions introduce one or more positive amino acid residues, such as arginine or lysine, in a position capable of forming a salt bridge with another amino acid in the sequence. In some embodiments, the amino acid substitutions or additions introduce one or more negative amino acid residues, such as aspartic acid or glutamic acid, in a position capable of forming a salt bridge with another amino acid in the sequence. In some embodiments, the amino acid substitutions or additions introduce both one or more positive and one or more negative amino acid residues in positions capable of forming one or more salt bridge with each other or with other amino acids in the sequence. In other embodiments, a salt bridge comprises one or more ionizable residues such as histidine, tyrosine or serine. In specific embodiments, the variant sequence comprises amino acid substitutions or additions that introduce one or more histidine residues and/or arginine residues and/or lysine residues and/or glutamic acid and/or aspartic acid residuces and/or tyrosine residues and/or serine residues in positions capable of forming one or more salt bridges.

In specific embodiments where the target protein is the Aβ protein, the peptide probe comprises the variant sequence of one of SEQ ID NOs:2-4 (Peptide 22, Peptide 38, or Peptide 45). In specific embodiments, the peptide probe consists of one of SEQ ID NOs:2-4. In other specific embodiments, the peptide comprises the variant sequence of one of SEQ ID NOs: 14-17 (Peptide 22 variation 1; Peptide 22 variation 2, Peptide 59, Peptide 77). In specific embodiments, the peptide consists of one of SEQ ID NOs: 14-17. In other embodiments, any of the other variants described herein may be further modified to include a salt bridge.

As noted above, the salt bridges can be designed to stabilize the alpha-helix conformation of the peptide. Additionally or alternatively, the presence of a salt bridge provides a mechanism for controlling the signal generated in an assay using the peptide. For example, the salt and/or pH of the assay buffer can be selected or adjusted to strengthen or weaken the salt bridge and thus control the stability of the alpha-helix conformation and the formation of β-sheet conformation.

B-Sheet Formation and Stability

In some embodiments, the variant sequence comprises one or more amino acid additions, deletions and/or substitutions that facilitate the adoption of the β-sheet conformation upon contact, binding or interaction with target protein (or under other conditions conducive to β-sheet formation), such that the variant sequence (or peptide comprising it) adopts the β-sheet conformation more efficiently than the reference sequence upon contact, binding or interaction with target protein (or under other conditions conducive to β-sheet formation). Such peptide probes may exhibit increased sensitivity for detecting target protein having a β-sheet conformation than the reference sequence. In some embodiments, the variant sequence comprises one or more amino acid substitutions found in a β-sheet forming region of a naturally occurring mutant, such as a mutant that exhibits an increase tendency to adopt a β-sheet conformation and/or form aggregates. For example, variants comprising one or more of the substitution I32S or E22P are useful in this context, such as SEQ ID NO:5 or 7. Other examples include variants comprising the substitution E22Q ("Dutch") or E22K ("Italian"), such as SEQ ID NO:11 or 12. In another embodiment, the variant substitution comprises one or more of the substitutions F19S and L34P, such as SEQ ID NO:8. Other variants can be derived from mutants known in the art, such as those disclosed in Murakami et al., J. Biol. Chem. 46:46179-46187, 2003. For example, variants may comprise one or more of the substitutions A21G, E22G ("Arctic"), and D23N. Examples of such variants include SEQ ID NOs:9, 10 or 13. Additionally, any variants described herein may further comprise one or more point mutations based on these or other known mutations. For example, variants based on the Peptide 22 variants may further comprise one or more point mutations, such as E22K, E22Q, or E22G. Examples of such variants include SEQ ID NOs: 19-21. In specific embodiments where the target protein is the Aβ protein, the peptide probe comprises the variant sequence of any one of SEQ ID NOs: 5, 7-13 or 18-21. In specific embodiments, the peptide probide consists of any one of SEQ ID NOs: 5, 7-13, or 18-21.

In other embodiments, the peptide probes have a variant sequence that comprises one or more amino acid additions, substitutions or deletions relative to the reference sequence, such that the variant sequence adopts a less ordered or decreased β-sheet conformation and/or increased alpha-helix conformation upon binding to target protein exhibiting a (β-sheet conformation. Examples of such variants include SEQ ID NO:2 (Peptide 22), SEQ ID NO:3 (Peptide 38), SEQ ID NO:4 (Peptide 45), SEQ ID NO:14 (Peptide 22 var. 1), and SEQ ID NO:15 (Peptide 22 var. 2). In specific embodiments where the target protein is the Aβ protein, the peptide probe comprises the variant sequence of any one of SEQ ID NOs:2-4 or 14-15. In specific embodiments, the peptide probe consists of any one of SEQ ID NOs:2-4 or 14-15.

In more specific embodiments, the variant sequence comprises one or more further amino acid additions, substitutions or deletions relative to the reference sequence, such that the (3-sheet structure of the variant sequence is less thermodynamically stable or strong than that of a probe consisting of the reference sequence. For example, the variant sequence of SEQ ID NO:2 may comprise one or more further substitutions such as F19S, S26D, H29D, I31D, L34D, and L34P, relative to the numbering wildtype sequence. See, for example, Peptides AD323 (SEQ ID NO:28); AD325 (SEQ ID NO:29); AD330 (SEQ ID NO:30); AD329 (SEQ ID NO:31); AD328 (SEQ ID NO:32); AD327 (SEQ ID NO:33); GM6 (SEQ ID NO:34); GM6 variation 1 (SEQ ID NO:35) in the Table below. Peptide 132S (SEQ ID NO:5) also may fall into this category. In specific embodiments where the target protein is the Aβ protein, the peptide probe may comprise the variant sequence of any one of SEQ ID NOs:5 or 28-35, or may consists of any one of SEQ ID NOs:5 or 28-35.

Increased Stability and/or Reduced Reactivity

In some embodiments, the variant sequence comprises one or more amino acid additions, deletions and/or substitutions that render the variant (or peptide comprising it) more stable in an oxidizing environment than the reference sequence. In some embodiments, one or more methionine residues, such as a C-terminal methionine residue, are replaced with a residue more resistant to oxidation, such as an alanine residue. In specific embodiments where the target protein is the Aβ protein, the peptide comprises the variant sequence of SEQ ID NO:6 (Peptide AD250). In specific embodiments, the peptide consists of SEQ ID NO:6. In other embodiments, any of the other variants described herein may be further modified by the replacement of a methionine residue, such as a C-terminal methionine residue, with a residue more resistant to oxidation, such as an alanine residue.

Solubility and/or Hydrophilicity

In some embodiments, the variant sequence comprises one or more amino acid additions, deletions and/or substitutions that render the variant (or peptide comprising it) more hydrophilic and/or more soluble in aqueous environments. For example, variants comprising one or more charged residues (such as glutamic acid and/or d-Arginine) at or near the C- and/or N-terminus exhibit increased hydrophilicity and solubility in aqueous solutions. For example, a variant sequence may comprise one, two, three or more N-terminal, C-terminal, or internal glutamic acid and/or d-Arginine residues. In specific embodiments where the target protein is the Aβ protein, the peptide probe may comprise the variant sequence of AD272 (SEQ ID NO:22), AD316 (SEQ ID NO:23), AD305 (SEQ ID NO:24), and AD271 (SEQ ID NO:26), or may consist of these sequences. In other embodiments, any of the other variants described herein may be further modified by the addition of one, two, three or more glutamic acid and/or d-Arginine residues at or near the N-terminus or C-terminus.

Additionally or alternatively, the peptide probe may be conjugated to a hydrophilic moiety, such as a water-soluble polyethylene glycol (PEG), such as PEG with a molecular weight of about 1, 5, 6, 10, 12, 15, 20, 25, 30 or 35 kDa, including PEG with a molecular weight of about 10 kDa ("PEG10"). An example of such a peptide probe comprising a wildtype β-sheet forming sequence (SEQ ID NO:1) is depicted in Table 1 in the examples below (AD274). Any variant or peptide probe described herein can be conjugated to a hydrophilic moiety.

AB Binding Motif

In some embodiments, the variant sequence comprises one or more amino acid additions, deletions and/or substitutions that provide an additional Aβ binding motif, such as a motif comprising the amino acid residues GxxEG (SEQ ID NO:25), where "X" represents any amino acid residue. Examples of such variant sequences include P59 (SEQ ID NO:17) and P77 (SEQ ID NO:16). In specific embodiments where the target protein is the Aβ protein, the peptide probe may comprise the variant sequence of any one of SEQ ID NOs: 16 or 17, or may consist of any one of SEQ ID NOs:16 or 17. In other embodiments, any of the other variants described herein may be further modified to include a GxxEG motif.

It will be understood that the peptides described herein may comprise one or more of any combination of the above-described additions, substitutions and deletions. In some embodiments, in addition to the above-described amino acid additions and substitutions, the peptide may comprise the addition or substitution of one or more amino acid residues to facilitate labeling. In some embodiments, the peptide comprises one or more lysine residues to facilitate labeling, such as labeling with a pyrene moiety. In some embodiments, the peptide comprises a lysine residues at or near its C-terminus, N-terminus, or both. For example, the peptide may comprises a lysine residues at its C-terminus, N-terminus, or both. In other embodiments, the lysine residues are at other sites in the peptide as may be suitable for labeling, as discussed above. In embodiments where the reference sequence comprises amino acid 16 (lysine) of the Aβ protein, that lysine residue can be used for labeling. In some embodiments, the peptide probes are labeled through a side chain on a C-terminal lysine.

In some embodiments, the peptide probes have a C-terminal amide group in place of the C-terminal carboxyl group.

In some embodiments, the variant sequence comprises one, two, three, four, five, six, seven, eight, nine or ten amino acid additions, substitutions or deletions relative to the reference sequence. In other embodiments, the variant sequence consists of about ten to about twenty five amino acids in length, and the variant sequence comprises one, two, three, four, five, six, seven, eight, nine or ten amino acid additions, substitutions or deletions relative to the reference sequence. In another embodiment, the variant sequence has about 99%, about 98%, about 97%, about 96%, about 95%, about 90%, about 85%, about 80%, about 75%, about 70%, about 66%, about 65%, about 60%, about 55%, about 50%, about 45%, about 40%, about 35%, about 30%, about 25%, about 20%, about 15%, or about 10% identity to the reference sequence. In some embodiments, the variant sequence has about 66% to about 97% identity to the reference sequence.

The suitability of any given peptide can be assessed by the methods described and illustrated below in the examples. For example, the ability of a peptide to adopt a β-sheet conformation can be assessed as illustrated in Examples 1 and 5. The ability of a peptide to bind to target protein and emit a signal can be confirmed as illustrated in Examples 3-5.

(ii) Labels

The probes disclosed herein may comprise one or more detectable labels. For example, the probe may be coupled or fused, either covalently or non-covalently, to a label. In some embodiments, the labels are selected to permit detection of a specific conformation of the probe, such as the conformation adopted when the probe associates with target protein. In this scenario, the label may emit a first signal (or no signal) when the probe is in a first, unassociated conformation (such as a primarily random coil/alpha-helix conformation or less organized or less dense form) and a second signal, or no signal (i.e., the probe is quenched) when the probe undergoes a conformational shift upon association with target protein (such as a primarily β-sheet conformation or more organized or more dense form). Complementary general principles apply for peptide probes that change from a more ordered to a less ordered conformation upon binding with target protein, with a first signal associated with the probe's first, unassociated conformation (such as a β-sheet conformation or more organized or more dense form), and a second signal, or no signal when the probe undergoes a conformational shift upon association with target protein (such as to a primarily random coil/alpha-helix conformation or less organized or less dense form), The first signal and second signal may differ in one or more attributes, such as intensity, wavelength, etc. In embodiments where the signal includes emission of light, the first signal and second signal may differ in excitation wavelength and/or emission wavelength. The signal generated when the probe undergoes a conformation shift may result from interactions between labels bound to the same probe and/or may result from interactions between labels bound to different probes.

In some embodiments, the labels and label sites are selected such that the labels do or do not interact based on the conformation of the probe, for example, such that the labels do not interact when the probe is in its unassociated conformation and do interact when the probe undergoes a conformation shift upon association with target protein, to generate a detectable signal (including quenching), or vice versa. This may be accomplished by selecting label sites that are further apart or closer together depending on the associated state of the probe, e.g., depending on whether the probe has undergone a conformation shift upon association with target protein. In some embodiments, the magnitude of the signal associated with the associated probe is directly correlated to the amount of target protein detected. Thus, the methods of the present invention permit detection and quantification of target protein.

For example, fluorescent labels, including excimer, FRET or fluorophore/quencher label pairs, may be used to permit detection of a specific conformation of the probe, such as the conformation adopted when the probe associates with target protein, such as misfolded Aβ protein. In these embodiments, the probe is labeled at separate sites with a first label and a second label, each being complementary members of an excimer, FRET or fluorophore/quencher pair. For example, excimer-forming labels may emit their monomeric signals when the probe is in its unassociated state, and may emit their excimer signal when the probe undergoes a conformation shift that brings the labels in closer physical proximity, upon association with the target protein. This is illustrated schematically in FIG. 10, top panel. Similarly, FRET labels may emit their FRET signal when the probe undergoes a conformation shift that brings the labels in closer physical proximity. This is illustrated schematically in FIG. 10, bottom panel B. On the other hand, fluorophore/quencher label pairs may emit the fluorophore signal when the probe is in its unassociated state, and that signal may be quenched when the probe undergoes a conformation shift that brings the labels in closer physical proximity. As noted above, the labels may be sited such that the opposite change in signal occurs when the probe undergoes a conformation shift upon association with the target protein.

Alternatively, for probes that change from a more ordered to a less ordered conformation upon association or binding with target protein, excimer-forming labels may emit their excimer signals when the probe is in its unassociated state, and may emit their monomer signal when the probe undergoes a conformation shift that reduces the labels' physical proximity, upon association with the target protein. This is illustrated schematically in FIG. 10, bottom panel A. Likewise, FRET labels may emit their FRET signal when the probe is in its unassociated state, and a different signal or no signal when the probe undergoes a conformation shift that reduces the labels' physical proximity. On the other hand, fluorophore/quencher label pairs may be quenched when the probe is in its unassociated state (where the labels are in close physical proximity) and may emit the fluorophore signal when the probe is in its unassociated state, that reduces the labels' physical proximity. Again, the labels may be sited such that the opposite change in signal occurs when the probe undergoes a conformation shift upon association with the target protein.

In some embodiments, the probe is endcapped (at one or both ends of the peptide) with a detectable label. In some embodiments, the probe comprises a detectable label at or near its C-terminus, N-terminus, or both. For example, the probe may comprise a detectable label at its C-terminus, N-terminus, or both, or at other sites anywhere that generate a signal when the probe undergoes a conformation shift upon association with Aβ protein aggregate associated with a target protein. Thus, for example, the label sites may be selected from (i) the N-terminus and the C-terminus; (ii) the N-terminus and a separate site other than the C-terminus; (iii) the C-terminus and a separate site other than the N-terminus; and (iv) two sites other than the N-terminus and the C-terminus. Label sites other than the N-terminus or C-terminus may be any site within the peptide probe, including one, two, three, four, five, or more residues removed from a terminal residue. Peptide probes AD272 (SEQ ID NO:22), AD316 (SEQ ID NO:23), AD305 (SEQ ID NO:24), AD271 (SEQ ID NO:26), and AD273 (SEQ ID NO:27) in Table 1 below are examples of peptide probes where one of the labels is near, but not at, a terminus. In these probes, the label sites are two or three residues from the N-terminus or C-terminus.

In some embodiments, the N-terminal label is provided on the amine group of the N-terminal amino acid residue. In other embodiments, the N-terminal label is provided on a side chain of an amino acid residue at or near the N-terminus, such as on a side chain of a lysine (K) residue at or near the N-terminus. The label site can be selected to alter the fluorescence properties of the peptide probe, and improve or optimize the signal to noise ratio. Peptide probes AD266 (SEQ ID NO:36) and AD268 (SEQ ID NO:37) depicted in Table 1 below are examples of peptide probes with the N-terminal label provided on a side chain of the first N-terminal lysine residue.

In some embodiments, the N-terminal label is provided on the N-terminal amine, and the C-terminal label is provided on a side chain of a C-terminal lysine residue. In other embodiments, the N-terminal label is provided on on a side chain of an N-terminal lysine residue, and the C-terminal label is provided on a side chain of a C-terminal lysine residue.

In one embodiment, pyrene moieties are present at or near each terminus of the probe and the ratio of the pyrene monomer signal to the pyrene excimer signal is dependent upon the conformation of the probe. For example, the monomer signal may predominate when the probe is in its unassociated state, and the excimer signal may predominate when the probe undergoes a conformation shift upon association with target protein (or the excimer signal may increase without necessarily becoming predominant), or vice versa. Thus, the ratio of the pyrene monomer signal to the pyrene excimer signal may be measured. Pyrene moieties present at other sites on the probe also may be useful in this context, as long as excimer formation is conformation dependent based on the associated or unassociated state of the peptide probe. Table 1 includes a number of peptide probes labeled with pyrene ("(PBA)") at or near each of the N-terminus and C-terminus.

The formation of excimers may be detected by a change in optical properties. Such changes may be measured by known fluorimetric techniques, including UV, 1R, CD, NMR, or fluorescence, among numerous others, depending upon the fluorophore label. The magnitude of these changes in optical properties is directly related to the amount of probe that has adopted the conformation associated with the signal, and so is directly related to the amount of target protein or structure present.

While these embodiments have been described in detail with regard to excimer pairs, those skilled in the art will understand that similar considerations apply to FRET and fluorophore/quencher pairs. Table 1 includes a number of peptide probes labeled with FRET or fluorophore/quencher pair labels at or near each of the N-terminus and C-terminus. For example, a peptide probe can be labeled at one terminus with pyrene and at the other terminus with a quencher such as the Dabcyl fluorescence quencher (4-(4-dimethylaminophenyl) diazenylbenzoic acid), as illustrated by AD326 (SEQ ID NO:43). Alternatively, a peptide probe can be labeled at one terminus with the fluorophore EDANS (5-(2'-aminoethyl)aminonaphthalene-1-sulfonic acid) and at the other terminus with a quencher such as Dabcyl, as illustrated by AD309 (SEQ ID NO:44), AD306 (SEQ ID NO:45), AD303 (SEQ ID NO:46), AD302 (SEQ ID NO 47), AD301 (SEQ ID NO:48), and AD300 (SEQ ID NO:49). Alternatively, a peptide probe can be labeled at one terminus with a Dansyl label (5-dimethylaminonaphthalene-1-sulfonyl) and at the other terminus with a tryptophan residue (Trp, W), to provide FRET pair labeling, as illustrated by AD295 (SEQ ID NO:50). Alternatively, a peptide probe can be labeled at one terminus with 5(6)carboxyfluorescein (FAM) and at the other terminus with EDANS as illustrated by AD294 (SEQ ID NO:51), AD293 (SEQ ID NO:52), AD292 (SEQ ID NO:53), AD291 (SEQ ID NO:54), and AD290 (SEQ ID NO:55). These illustrative peptide probes comprise wildtype and variant sequences described elsewhere herein, and demonstrate that any peptide probe described herein can be labeled with any label pair at a variety of label sites. In some embodiments, a label is conjugated to a lysine residue, including an N-terminal, C-terminal or internl lysine residue. In other embodiments, a label is conjugated to a glutamic acid residue, including an N-terminal, C-terminal or internl glutamic acid residue. In some embodiments, one label is conjugated to a lysine residue and another label is conjugated to a glutamic acid residue. Other combinations and permutations of label sites will be readily recognized by the skilled artisan, and are included in the invention.

Moreover, while these embodiments have been described with reference to the use two labels per peptide probe, it should be understood that multiple labels could be used. For example, one or more labels could be present at each labeling site, or multiple labels could be present, each at different labeling sites on the probe. In these embodiments, the labels may generate independent signals, or may be related as excimer pairs, FRET pairs, signal/quencher, etc. For example, one site might comprise one, two, three, four or more pyrene moieties and another site might comprise a corresponding quencher.

As noted above, the probes disclosed herein may comprise a detectable label. For example, the probe may comprise a peptide probe that is coupled or fused, either covalently or non-covalently, to a label. In some embodiments, the peptide probe is endcapped (at one or both ends of the peptide) with a detectable label. In some embodiments, the peptide comprises a detectable label at or near its C-terminus, N-terminus, or both. For example, the peptide may comprises a detectable label at its C-terminus, N-terminus, or both, or at other positions anywhere that generate a signal when the peptide adopts a β-sheet conformation, or other conformation associated with its associated state. In some embodiments, both the C-terminus and the N-terminus are endcapped with small hydrophobic peptides ranging in size from about 1 to about 5 amino acids. These peptides may be natural or synthetic, but are preferably natural (i.e., derived from the target protein). The signal generated when the peptide adopts a β-sheet conformation (or other target protein-associated conformation) may result from interactions between labels bound to the same peptide (intra-peptide) and/or may result from interactions between labels bound to different peptides (inter-peptide). For example, peptides in the β-sheet conformation may self-associate such that labels bound to different peptide molecules are in sufficient physical proximity to generate an inter-peptide signal.

In some embodiments, the labels are used to detect a specific conformation of the peptide, such as the β-sheet conformation or other target-protein-associated conformation. In this scenario, the label may emit a first signal (or no signal) when the peptide is in a first conformation (such as a random coil/alpha-helix conformation) and a second signal when the peptide is in a second conformation (such as a β-sheet conformation). As discussed above, complementary principles apply for peptide probes that change from a more ordered to a less ordered conformation upon binding with target protein, with a first signal associated with the probe's first, unassociated conformation (such as a β-sheet conformation or more organized or more dense form), and a second signal, or no signal when the probe undergoes a conformational shift upon association with target protein (such as to a primarily random coil/alpha-helix conformation or less organized or less dense form), The first signal and second signal may differ in one or more of intensity, wavelength, etc. In embodiments where the signal includes emission of light, the first signal and second signal may differ in excitation wavelength and/or emission wavelength.

Exemplary labels include fluorescent agents (e.g., fluorophores, fluorescent proteins, fluorescent semiconductor nanocrystals), phosphorescent agents, chemiluminescent agents, chromogenic agents, quenching agents, dyes, radionuclides, metal ions, metal sols, ligands (e.g., biotin, streptavidin haptens, and the like), enzymes (e.g., beta-galactosidase, horseradish peroxidase, glucose oxidase, alkaline phosphatase, and the like), enzyme substrates, enzyme cofactors (e.g., NADPH), enzyme inhibitors, scintillation agents, inhibitors, magnetic particles, oligonucleotides, and other moieties known in the art. Where the label is a fluorophore, one or more characteristics of the fluorophore may be used to assess the structural state of the labeled probe. For example, the excitation wavelength of the fluorophore may differ based on the structural state of the labeled probe. In some embodiments, the emission wavelength, intensity, or polarization of fluorescence may vary based on the structural state of the labeled probe.

As used herein, a "fluorophore" is a chemical group that may be excited by light to emit fluorescence or phosphorescence. A "quencher" is an agent that is capable of quenching a fluorescent signal from a fluorescent donor. A first fluorophore may emit a fluorescent signal that excites a second fluorophore. A first fluorophore may emit a signal that is quenched by a second fluorophore. The probes disclosed herein may undergo fluorescence resonance energy transfer (FRET).

Fluorophores and quenchers may include the following agent (or fluorophores and quenchers sold under the following tradenames): 1,5 IAEDANS; 1,8-ANS; umbelliferone (e.g., 4-Methylumbelliferone); acradinum esters, 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC8(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); a fluorescent protein (e.g., GFP (S65T); GFP red shifted (rsGFP); GFP wild type, non-UV excitation (wtGFP); GFP wild type, UV excitation (wtGFP); and GFPuv); Gloxalic Acid; Granular Blue; Haematoporphyrin; Hoechst 33258; Hoechst 33342; Hoechst 34580; HPTS; Hydroxycoumarin; Hydroxystilbamidine (Fluoro-Gold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; luminol, Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

In some embodiments, the label is a pyrene moiety. As used herein, a pyrene moiety includes pyrene, which comprises four fused benzene rings or a derivative of pyrene. By pyrene deriviative is meant a molecule comprising the four fused benzene rings of pyrene, wherein one or more of the pyrene carbon atoms is substituted or conjugated to a further moiety. Exemplary pyrene derivatives include alkylated pyrenes, wherein one or more of the pyrene carbon atoms is substituted with a linear or branched, substituted or unsubstituted, alkyl, alkenyl, alkynyl or acyl group, such as a $C_1$-$C_{20}$, linear or branched, substituted or unsubstituted alkyl, alkenyl, alkynyl or acyl group, where the group may be substituted with, for example, a moiety including an O, N or S atom (e.g., carbonyl, amine, sulfhydryl) or with a halogen. In some embodiments the pyrene derivative includes one or more free carboxyl groups and/or one or more free amine groups, each of which may be directly attached to a pyrene carbon atom or attached to any position on a linear or branched, substituted or unsubstituted, alkyl, alkenyl, alkynyl or acyl group as described above, such as being attached at a carbon atom that is separated from a pyrene carbon by 1 or more, such as 1 to 3, 1 to 5, or more, atoms. In some embodiments, the pyrene is substituted with one or more acetic acid moieties and/or one or more ethylamine moieties. In some embodiments, the pyrene derivative is substituted with a single methyl, ethyl, propyl or butyl group. In some embodiments, the pyrene is substituted with a short chain fatty acid, such as pyrene butyrate. In another embodiment, the pyrene is conjugated to albumin, transferring or an Fc fragment of an antibody. In some embodiments, the substituent is attached to pyrene through a carbon-carbon linkage, amino group, peptide bond, ether, thioether, disulfide, or an ester linkage. In other embodiments, the pyrene derivative is PEGylated pyrene, i.e, pyrene conjugated to polyethylene glycol (PEG). Such pyrene derivatives may exhibit a longer circulating half-life in vivo. In other embodiments, the pyrene derivative is pyrene conjugated to albumin.

In some embodiments, the label comprises a fluorescent protein which is incorporated into a peptide probe as part of a fusion protein. Fluorescent proteins may include green fluorescent proteins (e.g., GFP, eGFP, AcGFP, TurboGFP, Emerald, Azami Green, and ZsGreen), blue fluorescent proteins (e.g., EBFP, Sapphire, and T-Sapphire), cyan fluorescent proteins (e.g., ECFP, mCFP, Cerulean, CyPet, AmCyanl, and Midoriishi Cyan), yellow fluorescent proteins (e.g., EYFP, Topaz, Venus, mCitrine, YPet, PhiYFP, ZsYellowl, and mBanana), and orange and red fluorescent proteins (e.g., Kusabira Orange, mOrange, dTomato, dTomato-Tandem, DsRed, DsRed2, DsRed-Express (T1), DsREd-Monomer, mTangerine, mStrawberry, AsRed2, mRFP1, JRed, mCherry, HcRedl, mRaspberry, HcRed-Tandem, mPlum and AQ143). Other fluorescent proteins are described in the art (Tsien, R. Y., *Annual. Rev. Biochem.* 67:509-544 (1998); and Lippincott-Schwartz et al., *Science* 300:87-91 (2003)). As noted above, the probes may be comprised in fusion proteins that also include a fluorescent protein coupled at the N-terminus or C-terminus of the probe. The fluorescent protein may be coupled via a peptide linker as described in the art (U.S. Pat. No. 6,448,087; Wurth et al., *J. Mol. Biol.* 319:1279-1290 (2002); and Kim et al., *J. Biol. Chem.* 280:35059-35076 (2005), which are incorporated herein by reference in their entireties). In some embodiments, suitable linkers may be about 8-12 amino acids in length. In further embodiments, greater than about 75% of the amino acid residues of the linker are selected from serine, glycine, and alanine residues.

In embodiments comprising in vivo detection or imaging, labels useful for in vivo imaging can be used. For example, labels useful for magnetic resonance imaging, such as fluorine-18 can be used, as can chemiluminescent labels. In another embodiment, the probe is labeled with a radioactive label. For example, the label may provide positron emission of a sufficient energy to be detected by machines currently employed for this purpose. One example of such an entity comprises oxygen-15 (an isotope of oxygen that decays by positron emission) or other radionuclide. Another example is carbon-11. Probes labeled with such labels can be administered to a patient, permitted to localize at target protein, and the patient can be imaged (scanned) to detect localized probe, and thus identify sites of localized target protein. Labeled probes can be administered by any suitable means that will permit localization at sites of target protein, such as by direct injection, intranasally or orally. In some embodiments, radiolabeled probes can be injected into a patient and the binding of the probe to the protein target monitored externally.

In some embodiments, the label comprises an oligonucleotide. For example, the peptide probes may be coupled to an oligonucleotide tag which may be detected by known methods in the art (e.g., amplification assays such as PCR, TMA, b-DNA, NASBA, and the like).

4. Methods

The peptide probes described herein selectively associate with target protein and undergo a conformation shift upon association with target protein. For example, in some embodiments, the probes described herein bind to Aβ protein aggregates associated with a target protein and undergo a conformation shift upon such binding. As noted above, the conformation shift may comprise a change in the distance between the N- and C-termini of the probe (or between any other two points), folding more or less compactly, adopting a more ordered or less ordered conformation, changing from predominantly one secondary structure to predominantly another secondary structure, or any change in the relative amounts of different secondary structures. As noted above, "conformation shift" includes those shifts that can be detected by indirect means, such as through label signaling discussed below, even if more direct measures of conformation, such as CD, do not reveal a change in conformation.

In some embodiments, the probe undergoes a conformation change similar to that of the target protein. For example, in some embodiments, the probes are capable of adopting both a primarily random coil/alpha-helix conformation and a primarily β-sheet conformation, and adopt a primarily β-sheet conformation upon binding to target protein exhibiting a primarily β-sheet conformation. In some embodiments the probe is provided in a primarily α-helix/random coil conformation, and undergoes a conformation shift to a primarily β-sheet conformation upon contact, binding, association and/or interaction with target protein in a primarily β-sheet conformation. In other embodiments, the probe shifts conformation by becoming more condensed, more diffuse, or adopting any different configuration. In some embodiments, the probe more closely adopts the conformation of the Aβ protein aggregates. In other embodiments, the probes are capable of adopting both a primarily random coil/alpha-helix conformation and a primarily β-sheet conformation, and adopt a less ordered or reduced β-sheet conformation upon binding to target protein exhibiting a primarily β-sheet conformation. In these embodiments the probe may be provided in a primarily β-sheet conformation, and will undergo a conformation shift to a less ordered or reduced β-sheet conformation/increased random coil/alpha-helix conformation upon contact, binding, association and/or interaction with target protein in a primarily β-sheet conformation.

In some embodiments, the peptide probe preferentially bind to target protein in a specific state of self-aggregation, such as monomers, dimers, soluble oligomers (e.g., 4-12 mers), insoluble aggregates and fibrils (e.g., 100-1000 mers or larger). This is described generally in US 2008/0095706 (corresponding to U.S. patent application Ser. No. 11/828, 953), the entire contents of which are incorporated herein by reference in their entireties. This is illustrated with work done with Peptide 22 (SEQ ID NO:2).

FIG. 12 illustrates the specificity of Peptide 22 (SEQ ID NO:2) for soluble Aβ oligomers. The first two panels show the dose-dependent increase in pyrene monomer signal when Peptide 22 is incubated with soluble Aβ oligomers prepared by two different methods. The next two panels show no change in fluorescence when Peptide 22 is incubated with Aβ40 monomers and Aβ42 monomers. The next panel shows no change in fluorescence when Peptide 22 is incubated with Aβ40 fibers and the next panel shows some dose-dependent increase in monomer fluorescence when Peptide 22 is incubated with Aβ42 fibers. The last two panels show no change in fluorescence when Peptide 22 is incubated with control solutions (BSA or Anhydrase). Thus, Peptide 22 preferentially binds to Aβ protein in the form of soluble Aβ oligomers. Similar data has been obtained for Peptide 38 (SEQ ID NO:3), showing that it also preferentially binds to Aβ protein in the form of soluble Aβ oligomers.

The ability to detect soluble Aβ oligomers may have particular clinical significance because soluble oligomers are believed to be an active pathogenic form of Aβ protein. Moreover, the ability to detect soluble Aβ oligomers may permit detection, diagnosis and treatment earlier during the course of disease progression than is permitted by the detection of Aβ fibrils.

Thus, in accordance with some embodiments, there is provided a method for detecting target protein in a test sample, wherein the target protein exhibits a β-sheet conformation associated with an amyloidogenic disease, comprising: (i) contacting the sample with the peptide probe to form a test mixture; and (ii) detecting any binding between the peptide probe and any target protein present. In some embodiments, the method is effected in vitro.

A "test sample" is any sample to be tested and may be, inter alia, from human or animal tissue, blood, cerebrospinal fluid, urine, feces, hair, saliva or any other portion of the patient. In another embodiment, the test sample may be from any source that may contain biological material containing a target protein of interest, including pharmaceutical products, food products, clothing or other animal-derived material or environmental samples. The test sample may be prepared for use in the present methods in any manner compatible with the present methods, for example homogenization, cell disruption, dilution, clarification, etc. Care should be taken to not denature the proteins in the test sample so that the target protein retains its original conformation. The test sample may optionally be disaggregated prior to the addition of the peptide probe using conventional techniques, such as sonication. In embodiments related to in vivo detection, the test sample is a living subject.

For in vitro uses, the probe may be provided in a solution, such as an aqueous solution with a pH of between about 4 and about 10, such as between about 5 and about 8, with an ionic strength of between about 0.01 and about 0.5 (when typically prepared with a chloride salt, such as sodium chloride or potassium chloride). The solution may also comprise a water-miscible organic material (e.g., trifluoroethanol, hexafluoro-2-propanal (HFIP) or acetonitrile (ACN)) in amounts between about 30% to about 100% by volume, such as between about 45% to about 60%. The solvent may be prepared with a suitable buffering system such as acetate/acetic acid, Tris, or phosphate. For in vivo uses, the probe may be provided in any physiologically acceptable solution. For example, the probe may be prepared as a trifluoracetic salt and resuspended in an organic solvent, such as 100% HFIP or 50% ACN.

In other embodiments the method is effected in vivo and comprises administering the peptide probe to a subject and, for example, scanning the subject to detect labeled peptide probe localized at sites of β-sheet conformation target protein. Further details on in vivo methodologies are provided, for example, in US 2008/0095706, the contents of which are incorporated herein by reference in their entirety. In such in vivo embodiments, a labeled peptide probe can be administered to a patient, such as by local injection, allowed to localize at any sites of target protein or higher order target protein structures present within the patient, and then the patient can be scanned to detect the sites of labeled probe localized at sites of target protein or higher order target protein structures. Other routes of administration also are contemplated, including intranasal and oral. As discussed above, the probe can be labeled with any label suitable for in vivo imaging. The patient can be subject to a full body scan to identify any site of target protein. Alternatively, specific areas of the patient can be scanned to determine whether target protein is localized in the specific areas. Specific areas of interest may include vascular tissue, lymph tissue or brain (including the hippocampus or frontal lobes), or other organs such as the heart, kidney, liver or lungs. Exemplary suitable scanning or imaging techniques include positron emission tomography (PET), single photon emission computed tomography (SPECT), magnetic resonance imaging (MRI), radiography, tomography, fluoroscopy, nuclear medicine, optical imaging, encephalography and ultrasonography.

In some embodiments, such as for the detection of insoluble target protein (such as Aβ fibrils), binding between the peptide probe and target protein results in the formation of insoluble complexes. The insoluble complexes can be detected using conventional techniques, such as by separating the insoluble complex from the reaction mixture using conventional techniques such as centrifugation to pellet the insoluble complex and/or filtration. The insoluble complex can then be further characterized by techniques to detect, for example, any peptide probe present in the insoluble complex. Such detection techniques may include, for example, detecting the label of the peptide probe, or other techniques such by characterizing the insoluble complex using such techniques as SDS-PAGE, which separates proteins based on molecular weight, or other conventional techniques known in the art. Detection of the detectable label on the peptide probe in the insoluble complex is correlated with the presence of peptide probe-target protein complex, which in turn is correlated with target protein in the test sample.

In some embodiments, such as for the detection of soluble target protein aggregates (such as soluble Aβ oligomers) binding between the peptide probe and target protein results in the formation of soluble complexes. Detection of complexes including soluble complexes can be effected by several different methods. For example, the complexes can be separated from other constituents of the reaction mixture, such as unbound peptide probe and/or unbound target protein, and then the complexes can detected by detecting the detectable label on the peptide probe present in the complex. Separation can be accomplished using any method known in the art.

In some embodiments, the peptide probe-target protein complex is separated using size exclusion chromatography (SEC). SEC retains smaller molecules using pores or openings in the capture media (also termed stationary phase) such that the smaller molecules migrate more slowly through capture media while the larger molecules pass through more quickly. These pores or openings are of defined size and can be selected to differentiate between the peptide probe-target protein complex and unbound peptide probe and/or unbound target protein. In accordance with these methodologies, peptide probe-target protein complex will elute before unbound peptide probe. Detection of the detectable label on the peptide probe in earlier fraction(s) is correlated with the presence of peptide probe-target protein complex, which in turn is correlated with target protein in the test sample.

An alternative embodiment uses affinity chromatography to retain the peptide probe-target protein complex on the capture media. This approach utilizes a capture media, such as a solid phase, that comprises an affinity molecule that binds to the peptide probe-target protein complex. The affinity molecule can be selected to specifically bind the target protein, the peptide probe, the complex, or a label conjugated to any component of the peptide probe-target protein complex. In some embodiments, the affinity molecule specifically binds the target protein or a label conjugated to the target protein such that the target protein is retained on the capture media. Once unbound constituents (including any unbound peptide probe) is washed off, the bound material can be eluted, typically using an elution buffer, and the eluant can be analyzed. Detection of the detectable label on the peptide probe in the eluant is correlated with the presence of peptide probe-target protein complex in the eluant, which in turn is correlated with target protein in the test sample. In some embodiments, the target protein is conjugated to a moiety to which the affinity molecule of the capture media binds. For example, if the affinity molecule comprises avidin or streptavidin, the target protein may be conjugated to biotin.

In other embodiments, the peptide probe is conjugated to a moiety specifically bound by the affinity molecule, such as biotin. Such peptide probes are particularly suited for use in ELISAs and immunoprecipitation assays. For example, an avidin-coated plate can be used in conjunction with biotin-labeled peptide probes. After washing to remove non-specifically bound probe, a sample to be assayed for target protein is added. After washing to remove non-specifically bound substances, an antibody that specifically binds to the target protein is added (such as mouse anti-Aβ antibody, such as antibody 6E10 that recognizes Aβ protein, but not peptide probes). After washing to remove non-specifically bound antibody, a labeled antibody is added (such as horseradish peroxidase labeled mouse anti-IgG antibody). In such assays, detection of the antibody label is correlated with the presence of target protein in the sample.

Peptide probes AD310 (SEQ ID NO:38), AD313 (SEQ ID NO:39), AD314 (SEQ ID NO:40), AD317 (SEQ ID NO:41), and AD321 (SEQ ID NO:42) in Table 1 below illustrate specific embodiments of such peptide probes, with examples of alternative sites of biotinylation. While each of these peptide probes comprises SEQ ID NO:2 (Peptide 22), those skilled in the art will understand that any peptide probe described herein can be biotinylated as described in general above, and as illustrated specifically by these peptide probes. For example, biotinylation can be achieved through a helical linker (such as EAAAK; SEQ ID NO:56) at the C-terminus, as illustrated by AD310 (SEQ ID NO:38). In general, a helical linker includes residues that form alpha helices, such as alanine residues. Alternatively, biotinylation can be achieved through a side chain on a lysine residue, including an internal or terminal lysine residue, as illustrated by AD313 (SEQ ID NO:39). Alternatively, biotinylation can be achieved through a flexible linker (such as GSSGSSK (SEQ ID NO:57)) at the C-terminus, as illustrated by AD314 (SEQ ID NO:40). In general, a flexible linker includes one or more glycine and/or serine residues, or other residues that can freely rotate about their phi and psi angles. Alternatively, biotinylation can be achieved through a thrombin site linker (such as a linker comprising LVPRGS (SEQ ID NO:58), such as GLVPRGSGK (SEQ ID NO:59)) at the at the C-terminus, as illustrated by AD317 (SEQ ID NO:41). Alternatively, biotinylation can be achieved through a kinked linker (such as PSGSPK (SEQ ID NO:60)) at the at the C-terminus, as illustrated by AD321 (SEQ ID NO:42). In general, kinked linkers comprise one or more proline residues, or other residues that have fixed phi and psi angles that rigidly project the biotin moiety away from the peptide probe's protein-binding motif.

In some embodiments, binding between the peptide probe and target protein is detected by detecting a signal generated by the peptide probe, such as a signal generated when the peptide probe exhibits a β-sheet conformation or other conformation associated with its target protein-associated state. These embodiments may be effected in vitro or in vivo, either with (such as describe a above) or without (such as in in vivo embodiments) separation of peptide probe-target protein complex from the reaction mixture. In these embodiments, the peptide probe may be labeled with an excimer-forming label, such as pyrene, or with FRET labels. With either type of label, a signal is generated when the peptide probe adopts a β-sheet conformation or other conformation associated with its target protein-associated state, such as may occur upon contact, interaction or binding with target protein exhibiting a β-sheet conformation.

An excimer is an adduct that is not necessarily covalent and that is formed between a molecular entity that has been excited by a photon and an identical unexcited molecular entity. The adduct is transient in nature and exists until it fluoresces by emission of a photon. An excimer represents the interaction of two fluorophores that, upon excitation with light of a specific wavelength, emits light at a different wavelength, which is also different in magnitude from that emitted by either fluorophore acting alone. It is possible to recognize an excimer (or the formation of an excimer) by the production of a new fluorescent band at a wavelength that is longer than that of the usual emission spectrum. An excimer may be distinguished from fluorescence resonance energy transfer since the excitation spectrum is identical to that of the monomer. The formation of the excimer is dependent on the geometric alignment of the fluorophores and is heavily influenced by the distance between them.

In one embodiment, pyrene moieties are present at or near each terminus of the peptide probe and excimer formation between fluorophores is negligible as long as the overall peptide conformation is α-helix or random coil, but excimers are formed when the peptide agent undergoes a structural change (such as a conformational change to a β-sheet conformation) such that the pyrene moieties are brought into proximity with each other. Pyrene moieties present at other positions on the peptide also may be useful in this context, as long as excimer formation is conformation dependent. Further, the magnitude of excimer formation is directly related to the amount of protein analyte present. Thus, the methods of the present invention permit detection and in vivo imaging of a target protein or structure by detecting excimer formation.

Figure 11:
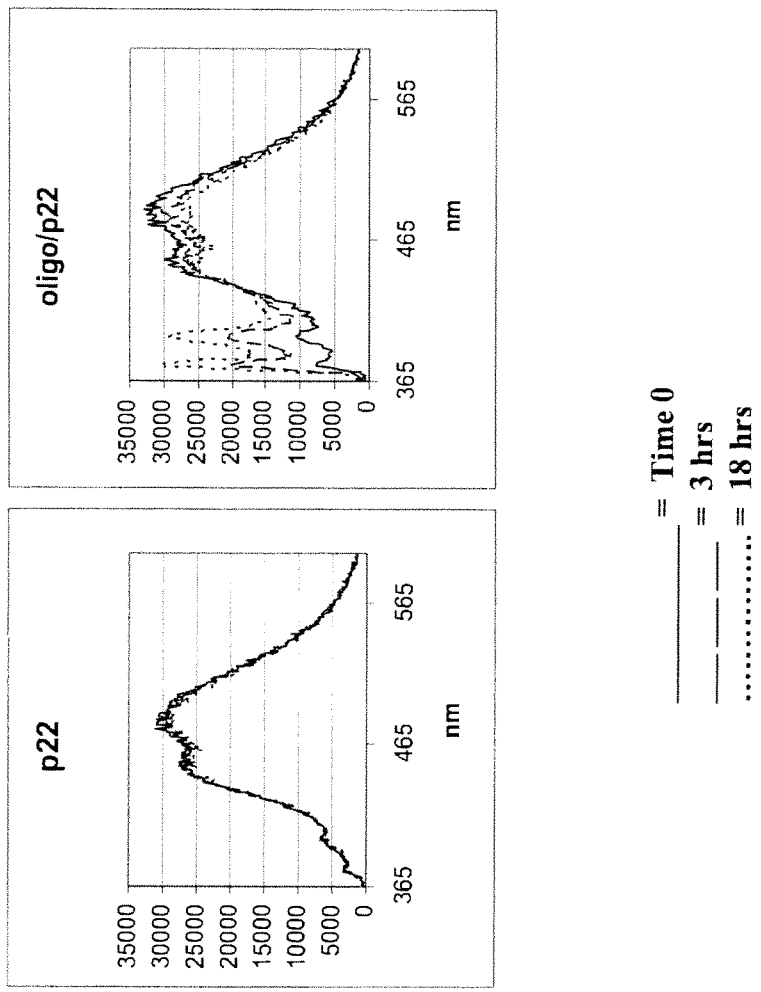
FIG. 11 illustrates raw fluorescence spectra for Peptide 22 (SEQ ID NO:2) labeled with pyrene at each terminus in the absence (left) and presence (right) of soluble Aβ oligomers.

In embodiments where the peptide probes change from a more ordered to a less ordered conformation upon association or binding with target protein, when pyrene moieties are present at or near each terminus of the peptide probe, the excimer signal may be the signal associated with the unassociated state of the peptides, and pyrene monomer fluoresce will be lower. When such peptides come into contact with target protein in a β-sheet conformation, they undergo a conformation change that decreases the physical proximity of the pyrene labels, resulting in a decreased pyrene excimer signal and an increased pyrene monomer signal, Pyrene moieties present at other positions on the peptide also may be useful in this context, as long as excimer/monomer signaling is dependent on a conformation that changes depending on whether the peptide probe is in an associated (e.g., bound) or unassociated (e.g., not bound to target protein) state. Further, in these embodiments, the increase of pyrene monomer signal, or the reduction in pyrene excimer signal, is directly related to the amount of target protein present. Thus, these embodiments likewise permit detection and in vivo imaging of a target protein or structure by monitoring excimer and monomer signaling. This is shown in FIG. 11, using Peptide 22 (described in more detail below). In particular, FIG. 11 illustrates raw fluorescence spectra for Peptide 22 (SEQ ID NO:2) labeled with pyrene at each terminus in the absence (left) and presence (right) of soluble Aβ oligomers. The flourescence of Peptide 22 is stable over time in the absence of oligomer (no increase in monomer or excimer flourescence), but exhibits an increase in pyrene monomer signal when incubated with soluble Aβ oligomers.

The formation of excimers may be detected by a change in optical properties. Such changes may be measured by known fluorimetric techniques, including UV, IR, CD, NMR, or fluorescence, among numerous others, depending upon the fluorophore attached to the probe. The magnitude of these changes in optical properties is directly related to the amount of conjugate that has adopted the structural state associated with the change, and is directly related to the amount of target protein or structure present.

Similar considerations apply to FRET. For example, the peptide probe can be labeled at or near each terminus with labels selected from the following FRET label pairs: DACIA-I/NBD, Marina Blue/NBD and EDANS/Fam (fluorescene). For peptide probes that change from a less ordered to a more ordered conformation upon association or binding with target protein, detection of a FRET signal is associated with the β-sheet conformation of the peptide probe, and correlated with the presence of target protein. For peptide probes that change from a more ordered to a less ordered conformation upon association or binding with target protein, detection of a FRET signal is associated with the unassociated state of the probes, while detection of a different (monomer) signal or no signal is correlated with the presence of target protein.

Similar considerations also apply to fluorophore/quencher labels, as discussed above.

As discussed above, the peptide probes described herein are designed to achieve enhanced performance in detection assays, such as by exhibiting reduced background signal. Thus, the peptide probes may be more sensitive and more reliable than a reference peptide in detecting target protein exhibiting a β-sheet conformation.

As noted above, the target protein may be associated with a disease or condition. Thus, detection of the target protein may be correlated with a diagnosis of, or risk for, the disease or condition. In some embodiments, the amount of target protein exhibiting a β-sheet conformation detected by the peptide probes described herein may be correlated with clinically relevant disease characteristics, such as disease progression or state, or predisposition to disease. In other embodiments, the methods described herein may be used to determine the amount of misfolded amyloid protein present in a patient, and/or the ratio of Aβ40 to Aβ42 protein, which characteristics are known to correspond disease progression in amyloidogenic diseases, such as AD.

The peptide probes described herein also are useful for identifying agents that inhibit the ability of the target protein to exhibit a β-sheet conformation, such as may be useful in a therapeutic context. In such methods, the agent is incubated with target protein and binding of the peptide probe with target protein exhibiting a β-sheet conformation is detected. By comparing the amount of peptide probe bound to the target protein with and without incubation with the agent, the inhibitory ability of the agent can be determined. Exemplary methods are described in US 2008/0095706 (corresponding to U.S. patent application Ser. No. 11/828, 953), the entire contents of which are incorporated herein by reference in their entireties.

5. In Vivo Therapeutic Methods

In other embodiments, there is provided in vivo methodology for preventing the formation of protein aggregates of a target protein, comprising contacting the target protein in vivo with a peptide probe for the target protein, wherein the peptide probe preferentially binds to the target protein, thereby preventing the formation of higher order protein aggregates of the target protein. In some embodiments, the peptide probe preferentially binds to the target protein in a specific state of self-aggregation selected from the group consisting of monomers, soluble oligomers, and insoluble self-aggregates.

In accordance with other embodiments, there is provided methodology for delivering a therapeutic agent to a target protein, comprising combining the therapeutic agent with a peptide probe for the target protein and administering the peptide probe-therapeutic agent combination to a patient in need thereof. For example, a peptide probe can be conjugated (directly or through a linker) to a therapeutic agent for targeting delivery of the therapeutic agent to sites of target protein. In such in vivo embodiments, which are disclosed in US 2008/0095706 mentioned above, a peptide probe (alone or as a combination comprising another therapeutic agent) can be administered to a patient, such as by local injection, and allowed to localize at any sites of target protein or higher order target protein structures present within the patient, to effect therapy. Other routes of administration also are contemplated, including intranasal and oral. Specific areas of interest may include vascular tissue, lymph tissue or brain (including the hippocampus or frontal lobes), or other organs such as the heart, kidney, liver or lungs.

6. Kits

Also provided are kits comprising the peptides described herein. The kits may be prepared for practicing the methods described herein. Typically, the kits include at least one component or a packaged combination of components useful for practicing a method. By "packaged combination" it is meant that the kits provide a single package that contains a combination of one or more components, such as peptide probes, buffers, instructions for use, and the like. A kit containing a single container is included within the definition of "packaged combination." The kits may include some or all of the components necessary to practice a method disclosed herein. Typically, the kits include at least one peptide probe in at least one container. The kits may include multiple peptide probes which may be the same or different, such as probes comprising different sequences and/or different labels, in one or more containers. Multiple probes may be present in a single container or in separate containers, each containing a single probe.

EXAMPLES

Example 1

Figure 1B:
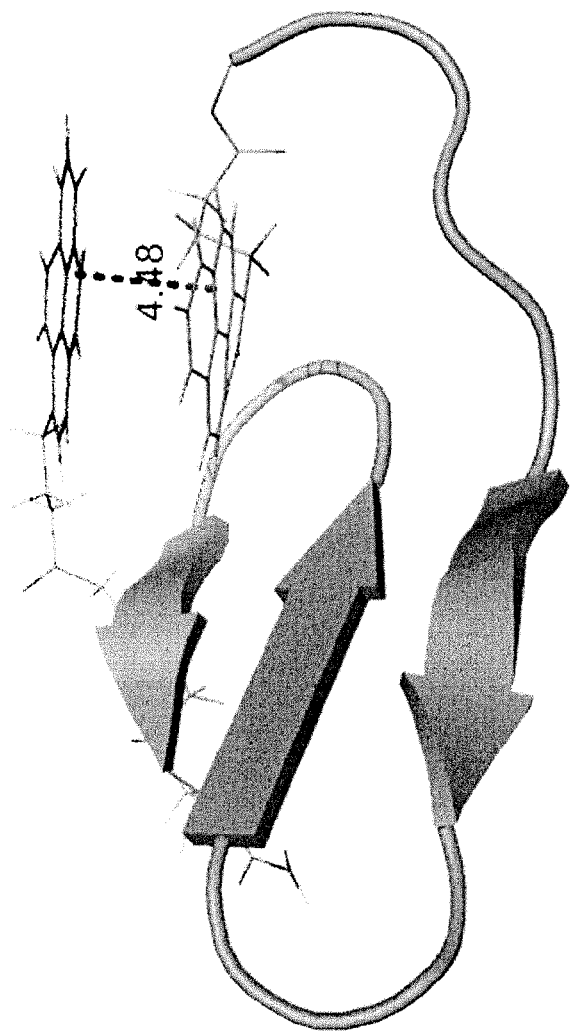
FIG. 1B illustrates the close physical proximity of pyrene moieties conjugated to the N- and C-termini of a peptide when the peptide is in a β-sheet conformation.
Figure 1C:
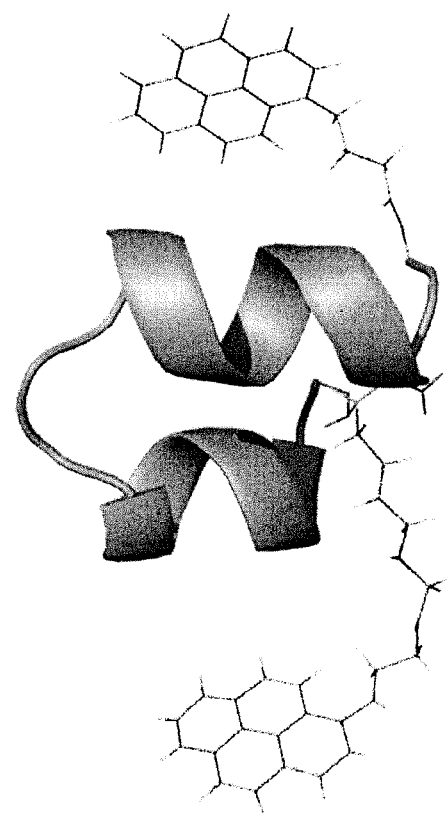
FIG. 1C illustrates the distance between pyrene moieties conjugated to the N- and C-termini of a peptide when the peptide is in a random coil/alpha-helix conformation.

Conjugation of fluorescent reporter moieties to peptides can provide a simple mechanism to monitor the conformational dynamics of a peptide under different solvent conditions, or in the presence of interaction partners (such as target proteins) and cofactors (such as anti-amyloid agents). As discussed above, pyrene emits two distinct fluorescent profiles depending on whether pyrene is in a monomeric state or if it is in close physical proximity to or paired with other pyrene molecules (excimeric state). When pyrene is conjugated at or near the N- and C-termini of a peptide described herein, the pyrene moieties may be separated by different distances depending on the conformation of the peptide, with the pyrenes in close physical proximity in the β-sheet conformation (FIG. 1B) and further apart in the random coil/alpha-helix conformation (FIG. 1C). Thus, when pyrene is conjugated at or near the N- and C-termini of a peptide described herein it can provide a fluorescent signal with two distinct fluorescent profiles depending on the conformation of the peptide, with the monomeric signal being associated with a random/coil alpha-helix conformation of the peptide, and the excimeric signal being associated with a β-sheet conformation of the peptide. Results can be reported as the signal of the β-sheet conformation (excimer) or as the fluorescence ratio of signal from the β-sheet conformation (excimer) and the signal from the alpha-helical conformation (monomer).

In silico modeling can be used to predict inter-pyrene distances when more than one pyrene moieties are conjugated to the peptides of interest, in order to select peptides that will yield different signals depending on the conformation of the peptide. FIG. 1A illustrates the in silico predictions for the distribution of inter-pyrene distances of pyrenes conjugated to each terminus of a peptide corresponding to a region of the Aβ peptide (SEQ ID NO:1), depending on the solvent environment of the peptide, at room temperature. As shown in this figure, the peptide adopts a β-sheet conformation in water, with the pyrene moieties in relatively close proximity (about 10 Å between the centers of the N- and C-terminal pyrene rings). In contrast, the peptide adopts an alpha-helix conformation in 40% trifluoroethanol (TFE), with the pyrene moieties further apart (about 20 Å between the centers of the N- and C-terminal pyrene rings).

Example 2

Novel peptide probes were designed in accordance with the principles described herein. As illustrated in FIG. 2, the peptide sequences are based on amino acids 17-35 of the Aβ peptide, which is a β-sheet forming region of the Aβ peptide. The reference sequence (WT; SEQ ID NO:1) corresponds to the wildtype sequence, with a terminal lysine residue added to facilitate pyrene labeling.

Peptide 22 (SEQ ID NO:2) includes a substitution with a histidine residue, a substitution with a glutamic acid residue, and the addition of a C-terminal lysine residue.

Peptide 38 (SEQ ID NO:3) includes a substitution with four consecutive alanine residues, a substitution with a histidine residue, a substitution with a glutamic acid residue, and the addition of a C-terminal lysine residue.

Peptide 45 (SEQ ID NO:4) includes the addition of three consecutive N-terminal alanine residues, a substitution with a histidine residue, a substitution with a glutamic acid residue, and the addition of a C-terminal lysine residue.

Peptide I32S (SEQ ID NO:5) includes the substitution of an isoleucine residue with a leucine residue and the addition of a C-terminal lysine residue.

Peptide M35A (SEQ ID NO:6) includes the substitution of a C-terminal residue with an alanine residue, and the addition of a lysine residue as the C-terminal residue of the peptide.

Peptide E22P (SEQ ID NO:7) includes the substitution of a glutamic acid residue with a proline residue.

Peptide GM6 (SEQ ID NO:8) includes the substitution of a phenylalanine residue with a serine residue as well as a leucine residue with a proline residue.

As discussed above, the histidine and glutamic acid residue substitutions in Peptides 22, 38 and 45 (SEQ ID NOs. 2-4) permit the formation of a salt bridge between those residues, which may stabilize the alpha-helix conformation and/or provide a means for controlling the signal generated by controlling assay conditions. As discussed above, these peptides exhibit reduced background signal because the peptide is less likely to adopt a β-sheet conformation in the absence of target protein in a β-sheet conformation.

As discussed above, the consecutive alanine substitutions (alanine repeats) in Peptide 38 (SEQ ID NO:3) and Peptide 45 (SEQ ID NO:4) have a high alpha-helical propensity, and thus stabilize the alpha-helix conformation of the peptide. Again, these peptides exhibit reduced background signal because the peptide is less likely to adopt a β-sheet conformation in the absence of target protein in a β-sheet conformation.

As discussed above, some substitutions facilitate the adoption of the β-sheet conformation, or other conformation change, upon contact, binding or interaction with target protein, such that the peptide adopts the β-sheet conformation, or undergoes a conformation change, more efficiently than the reference sequence upon contact, binding or interaction with target protein. The substitutions alanine to glycine, glutamic acid to proline glycine, glutamine, or lysine, and aspartic acid to asparagine in SEQ ID NOs:7, 9-13 and 19-21 result in peptide probes with enhanced β-sheet formation and aggregation properties.

The C-terminal methionine substitution in Peptide M35A (SEQ ID NO:6) renders the peptide more stable in an oxidizing environment than the reference (wildtype) sequence.

Additional work has shown that the isoleucine to serine substitution in Peptide I32S (SEQ ID NO:5), the serine, histidine, isoleucine, and/or leucine to aspartic acid substitutions in peptides AD323, AD325, AD330, AD329, AD328, and AD327 (SEQ ID NOs: 28-33), and the phenylalanine to serine and leucine to phenylalanine substitutions in peptides GM6 and GM6 variation 1 (SEQ ID NOs: 34-35) destabilize the β-sheet conformation of the resulting probes, although these probes may undergo a conformation change more efficiently than the reference (wildtype) sequence upon contact, binding or interaction with target protein, such as Aβ oligomers.

Example 3

Peptide probes can be used against a known target protein in several different assays to assess their suitability for use in a given assay and/or for use under given assay conditions. For example, one peptide may be more effective in one particular assay, while a different peptide may be more effected in a different assay. A peptide of SEQ ID NO:1 was used in several different assays, as described below. Similar assays can be used to detect target protein in a test sample.

(i) Insoluble Complexes

In this assay, soluble peptide probes are combined with insoluble target protein fibers in an in vitro centrifugation-based interaction assay. Peptide probe that binds to the target protein will be detected in an insoluble pellet, which may be isolated using centrifugation. Peptide probe that does not bind to the insoluble target protein fibers remains in the supernatant and is not detected in the pellet.

Figure 3:
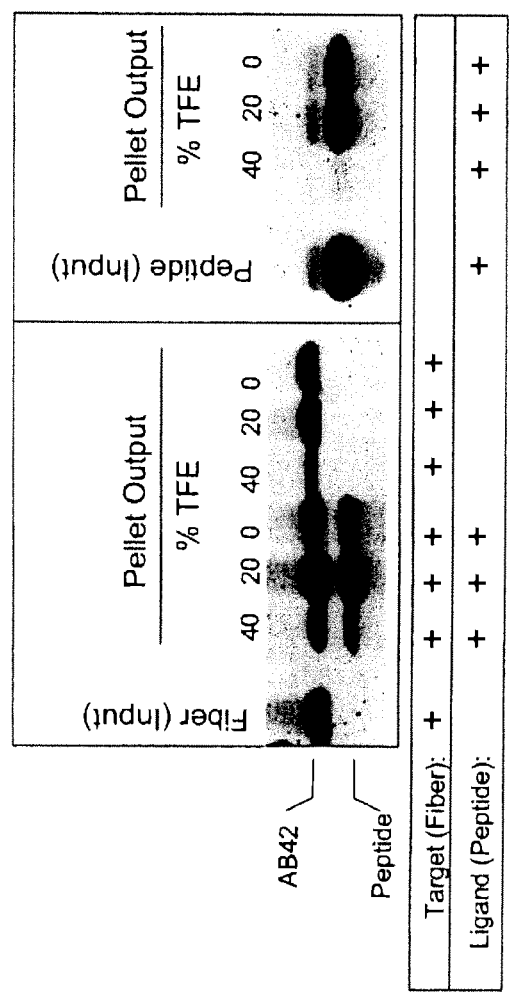
FIG. 3 illustrates the results of an in vitro centrifugation-based interaction assay using a peptide probe (SEQ ID NO:1) to detect insoluble Aβ42 target protein fibers.

Aβ42 Fiber (target protein) and peptide probe (SEQ ID NO:1) are incubated for 3 hours in the presence of increasing amounts of trifluoroethanol (TFE). The samples are centrifuged at 17,000×g for 30 minutes, and the pellets are denatured in sample buffer and analyzed by SDS-PAGE. Results are shown in FIG. 3. Reference samples (Input) are shown for comparison. In this example, binding of target protein and peptide probe is clearly observed at the 40% TFE condition (compare left and right panels at 40% TFE, where the "peptide" band appears in the left panel but not the right panel). This indicates that the peptide came down into the spun pellet with the fibril form of the target protein, which is shown as monomer Aβ42 on the SDA-PAGE because the fibril dissolves into monomer under SDS-PGE conditions.

If the peptide were labeled with a detectable label, a signal in the pelleted insoluble complex would correlate with target-peptide binding (not shown).

(ii) Size Exclusion Chromatography

In this assay, soluble peptide probes are combined with, for example, soluble target protein oligomers in an in vitro size exclusion chromatography-based interaction assay.

Labeled peptide probe (SEQ ID NO:1, 2 µM) and target protein (Aβ oligomers, 2 µM) are incubated together for 90 minutes in Hepes buffer (10 mM, pH 7.0) and then loaded onto a G25 size exclusion column, which has a 5000 Da molecular weight cutoff. The column is subjected to centrifugation at 735×g for 2 minutes. Eluants and column material are analyzed by a TECAN fluorimeter. This method is illustrated in FIG. 14A. Eluant also may be analyzed by SDS-PAGE (not shown).

In this assay, unbound peptide probe will remain on the column due to its small size. Thus, the detection of labeled peptide probe in the eluant indicates the presence of target protein-peptide complexes in the eluant. This is confirmed by the results illustrated in FIG. 14B, which show that the fluorescently labeled peptide is recovered in the presence of the oligomer.

In a similar assay with Peptide 45, labeled peptide probe (SEQ ID NO:4, 2 µM) and target protein (Aβ oligomers, 2 µM) are incubated together for 90 minutes in Hepes buffer (10 mM, pH 7.0) and then loaded onto a G25 size exclusion column, which has a 5000 Da molecular weight cutoff. The column is subjected to centrifugation at 735×g for 2 minutes. Eluants and column material are analyzed by a TECAN fluorimeter. This method is illustrated in FIG. 4A. In this assay, unbound peptide probe will remain on the column due to its small size. Thus, the detection of labeled peptide probe in the eluant indicates the presence of target protein-peptide complexes in the eluant. This is confirmed by the results illustrated in FIG. 4B, which show that the fluorescently labeled peptide is recovered in the presence of the oligomer.

(iii) Affinity Chromatography

In this assay, soluble peptide probes are combined with, for example, soluble target protein oligomers in an in vitro affinity chromatography-based interaction assay.

Figure 5A:
FIGS. 5A and 5B illustrate an in vitro affinity chromatography-based interaction assay using a labeled peptide probe (SEQ ID NO:2) to detect biotin-labeled soluble Aβ42 target protein oligomers, with results illustrated in FIG. 5B, which shows that labeled peptide probe is only detected in the captured material, in the presence of high molecular weight oligomers, indicating that the peptide probe binds the target protein oligolmers. Similar results were obtained with a labeled peptide probe of SEQ ID NO:1, as shown in FIG. 15.

For this example, target protein is labeled with an affinity molecule, such as biotin, and incubated with a labeled peptide probe. After incubation, the mixture is incubated with the capture moiety, such as streptavidin, on a support, for example a column or beads, such that the target protein is captured. After washing of unbound material, the support can be examined for detection of the labeled peptide probe, which would indicate the presence of bound target protein-peptide probe complexes on the support. Alternatively, the bound material may be eluted and then examined for detection of the labeled peptide probe. Again, detection of the labeled peptide probe would indicate the presence of target protein-peptide probe complexes in the eluant. FIGS. 5A and 15A illustrate an affinity chromatography assay using biotin-labeled target protein and streptavidin-coated beads. This type of assay is useful, for example, for assessing the efficacy of a given peptide probe.

Labeled peptide probe (SEQ ID NO:1, 2 µM) and biotinylated target protein (Aβ42 oligomers, 2 µM) are incubated in PBS for 30 minutes. The mixture is then subjected to a capture step using magnetic beads coated with streptavidin. The beads are washed with PBS to remove unbound material and the captured material is analyzed by SDS-PAGE.

In an alternative assay (protocol B, illustrated in FIG. 15A), 4 µN biotinylated Aβ42 oligomer was incubated with pre-washed streptavidin dynabeads at room temperature for 30 minutes. The complex was then washed two times with PBS buffer, and resuspended in PBS buffer. Equal volumes of bound oligomer and 4 µM labeled peptide probe (SEQ ID NO:1) were then combined, and incubated for 30 minutes at room temperature. Unbound material was then washed away with three PBS washes, followed by the collection of the bead complexes by magnet. The complex was then resuspended in 1×LDS buffer, boiled for 10 minutes, and loaded on 10% Bis-Tris gels.

FIG. 15B illustrates the results. As shown in the Figure, labeled peptide probe is only detected in the captured material, in the presence of high molecular weight oligomers, indicating that the peptide probe binds the target protein oligolmers. The captured material also could be analyzed by fluorescent profile (not shown).

In a similar assay with Peptide 22 (protocol A), labeled peptide probe (SEQ ID NO:2, 4 µM) and biotinylated target protein (Aβ42 oligomers, 4 µN) are incubated in Hepes buffer (10 mM, pH 7.0) for 90 minutes. The mixture is then subjected to a capture step using magnetic beads coated with streptavidin. The beads are washed with PBS to remove unbound material and the captured material is analyzed by SDS-PAGE.

In an alternative assay with Peptide 22 (protocol B, illustrated in FIG. 5A), 4 µN biotinylated Aβ42 oligomer was incubated with pre-washed streptavidin dynabeads at room temperature for 30 minutes. The complex was then washed two times with PBS buffer, and resuspended in PBS buffer. Equal volumes of bound oligomer and 4 µM labeled peptide probe (SEQ ID NO:2) were then combined, and incubated for 30 minutes at room temperature. Unbound material was then washed away with three PBS washes, followed by the collection of the bead complexes by magnet. The complex was then resuspended in 1×LDS buffer, boiled for 10 minutes, and loaded on 10% Bis-Tris gels.

Figure 5B:
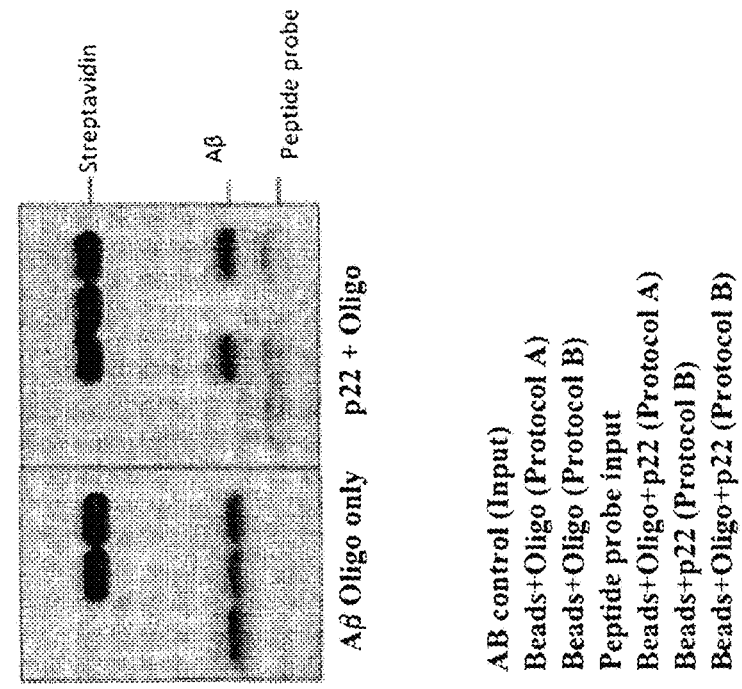

FIG. 5B illustrates the results. The left panel (lanes 1-3) shows that the magnetic streptavidin beads pull down synthetic biotinylated oligomer (compare lanes 2 and 3 to lane 1). Lane 4 shows the peptide probe (Peptide 22) loaded directly on the gel at a concentration of 4 µM, analogous to 100% binding. Lane 2 shows the binding reaction (Protocol A) loaded onto the gel—note that Aβ oligomer and peptide probe co-elute. Lanes 3 and 4 show binding reactions prepared according to Protocol B without (Lane 3) and with (Lane 4) the addition of biotinylated Aβ42 oligomer. In the absence of oligomer, the peptide probe is not present on the gel, indicating that it has not been bound to the streptavidin bead. In the presence of biotinylated oligomer, the peptide probe is recovered. These results show that the peptide probed directly binds to biotinylated Aβ42 oligomer.

Example 4

As discussed above, in some embodiments, the variant sequence of the peptide probe is designed to increase the signal difference between any signal associated with peptide that is not bound to target protein and a signal associated with peptide that is bound to target protein, such as by increasing the signal difference between any signal associated with the (unbound) random/alpha-helix conformation of the peptide (e.g., background signal) and a signal associated with the (bound) β-sheet conformation of the peptide. One way to assess this parameter is to incubate the labeled peptide in varying concentrations of TFE, which is an organic solvent that induces alpha-helical conformations in peptides. Peptides with a significant difference in signal between its alpha-helix and β-sheet conformations may be particularly useful for the reasons discussed above.

Peptide Probe 22 (SEQ ID NO:2, 2 μM) labeled at each terminus with pyrene is incubated in 0 to 80% TFE in tris buffer (10 mM Tris, pH 7.0) for 30 min. The reaction is measured by TECAN fluorimeter, and the excimer:monomer fluorescence ratio is recorded. As shown in FIG. 6A, the maximal signal response of Peptide 22 in buffer (signal gain from 80 to 20% TFE) is approximately 100 ratio units, which is 4 times greater than that of the reference peptide (SEQ ID NO:1). When tested for the ability to undergo conformational change in the presence of a fibrillar amyloid target protein, Peptide 22 performs 2.6 times greater than the reference peptide (SEQ ID NO:1). That is, Peptide 22 exhibits a maximal signal gain in the presence of fibrillar amyloid target protein that is about 2.6 times greater than the maximal signal gain of the reference peptide.

Example 5

(i) Structural Analysis of Peptide Probe Conformation

As discussed in Example 2, histidine and glutamic acid residue substitutions were introduced into Peptides 22, 38 and 45 (SEQ ID NOs: 2-4) so as to permit the formation salt bridges between those residues. CD analysis can be performed on such peptides under different pH and salt conditions to determine the conformation of the peptide under given conditions.

Figure 7:
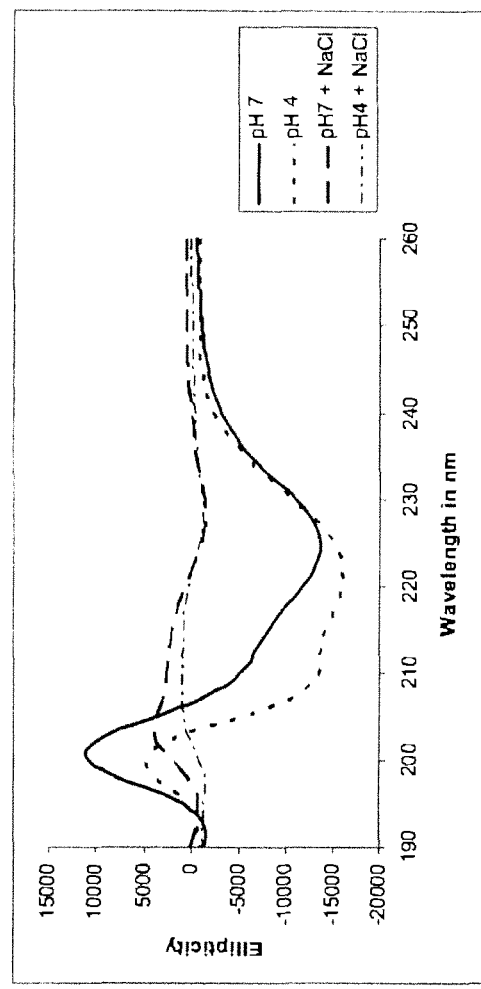
FIG. 7 illustrates the effect of pH and salt concentration on the secondary structure of Peptide 38 (SEQ ID NO:3) as determined by circular dichroism spectropolarimetry (CD) analysis.

Peptide 38 (SEQ ID NO:3) labeled at each terminus with a pyrene moiety is used in this example. As shown in FIG. 7, at pH 7 (solid line), the peptide is highly alpha helical (38%), and the proportion of alpha helix conformation is even greater at pH 4 (small dashed line) (52%). The addition of 500 mM NaCl greatly diminishes the alpha helix conformation in favor of a β-sheet conformation, at both pH levels. Thus, at pH 7, in the presence of 500 mM NaCl (large dashed line), the alpha helix content is 4%, while the fβ-sheet content is 40% (up from 10% without the salt). At pH 4, in the presence of 500 mM NaCl (dashed/dot line), the alpha helix content is 6%, while the β-sheet content is 52% (up from 4% without the salt). These results indicate that the salt bridge stabilizes the α helix conformation, the formation of which is favored at low pH and low salt. At greater salt concentrations, the salt bridge is destroyed, and the α helical conformation is no longer stabilized.

(ii) Structural Analysis of Peptide Probe Bound to Target Protein

Figure 8:
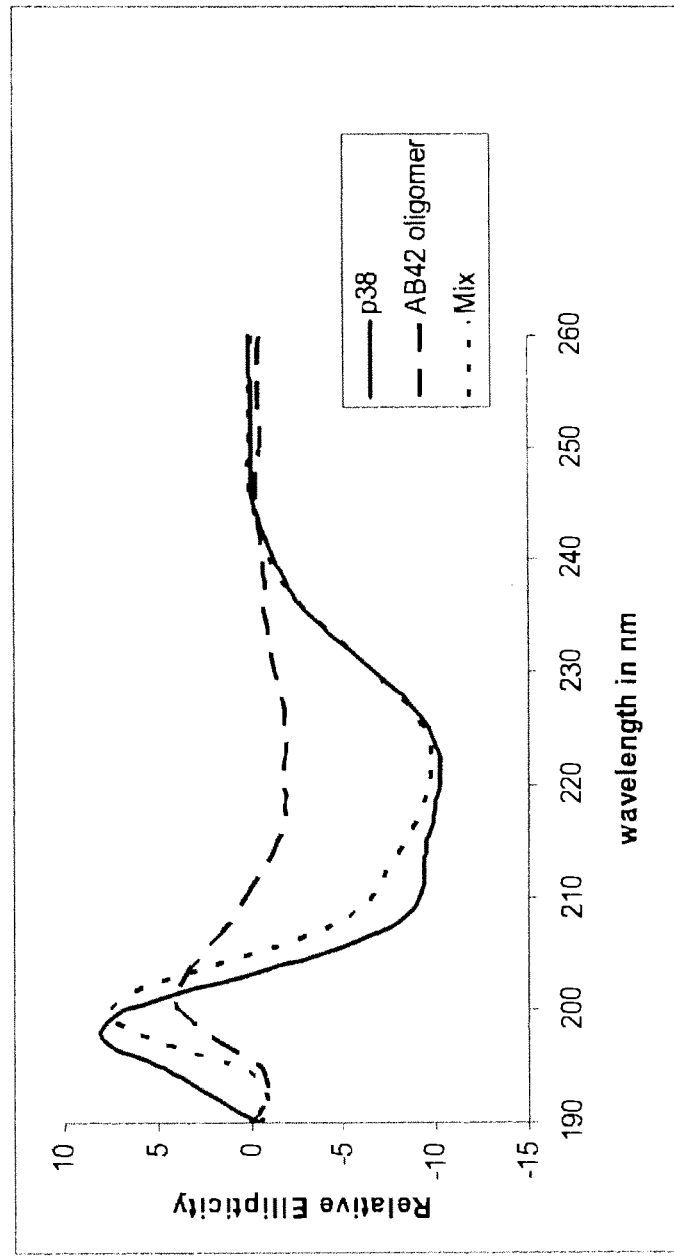
FIG. 8 illustrates the effect of the interaction of Aβ42 oligomer (target protein) on the secondary structure of Peptide 38 (SEQ ID NO:3) as determined by CD analysis.

The conformation of the peptide probe bound to the target protein can be assessed by CD analysis. FIG. 8 shows the conformation of di-pyrene labeled Peptide 38 (SEQ ID NO:3) and Aβ42 oligomer (target protein), each separately as well as in combination. The peptide alone is highly alpha helical (36%). Upon mixing of Peptide 38 with the target protein, the peptide undergoes a conformation shift that results in increased β-sheet conformation, and decreased α helix conformation. That is, the secondary structure of Peptide 38 is altered such that the proportion of a helix is halved (18%), while the proportion of β-sheet structure is enhanced from 20% to 31%. Thus, Peptide 38 adopts a β-sheet conformation upon contact with the Aβ42 oligomer target protein, and that conformation change can be detected by CD analysis.

(iii) Excimer Analysis of Peptide Probe Bound to Target Protein

The conformation of peptide probe bound to the target protein can also be detected by measuring pyrene fluorescence, on the peptide alone and in combination with the target protein. FIG. 9B shows the pyrene fluorescence of free di-pyrene labeled Peptide 45 (SEQ ID NO:4). The excimer fluorescence associated with the β-sheet conformation has a different wavelength than the monomer fluorescence associated with the alpha-helix conformation, and the excimer: monomer fluorescence ratio is 9:1. FIG. 9A shows the pyrene fluorescence of the di-pyrene labeled Peptide 45 in the presence of different amounts of Aβ42 oligomer target protein (0, 0.03, 0.1 and 0.3 μM). The addition of Aβ42 oligomer target protein results in a dose-dependent shift of the excimer:monomer fluorescence ratio to 20:1 at the highest Aβ42 oligomer concentration (0.3 μM). This change in excimer:monomer fluorescence ratio reflects a corresponding conformational change in the peptide, that results in increased β-sheet conformation, and decreased α helix conformation. Thus, Peptide 45 adopts a β-sheet conformation in a dose-dependent manner upon contact with the Aβ42 oligomer target protein, and that conformation change can be detecting by measuring pyrene fluorescence.

Example 6

Figure 10:
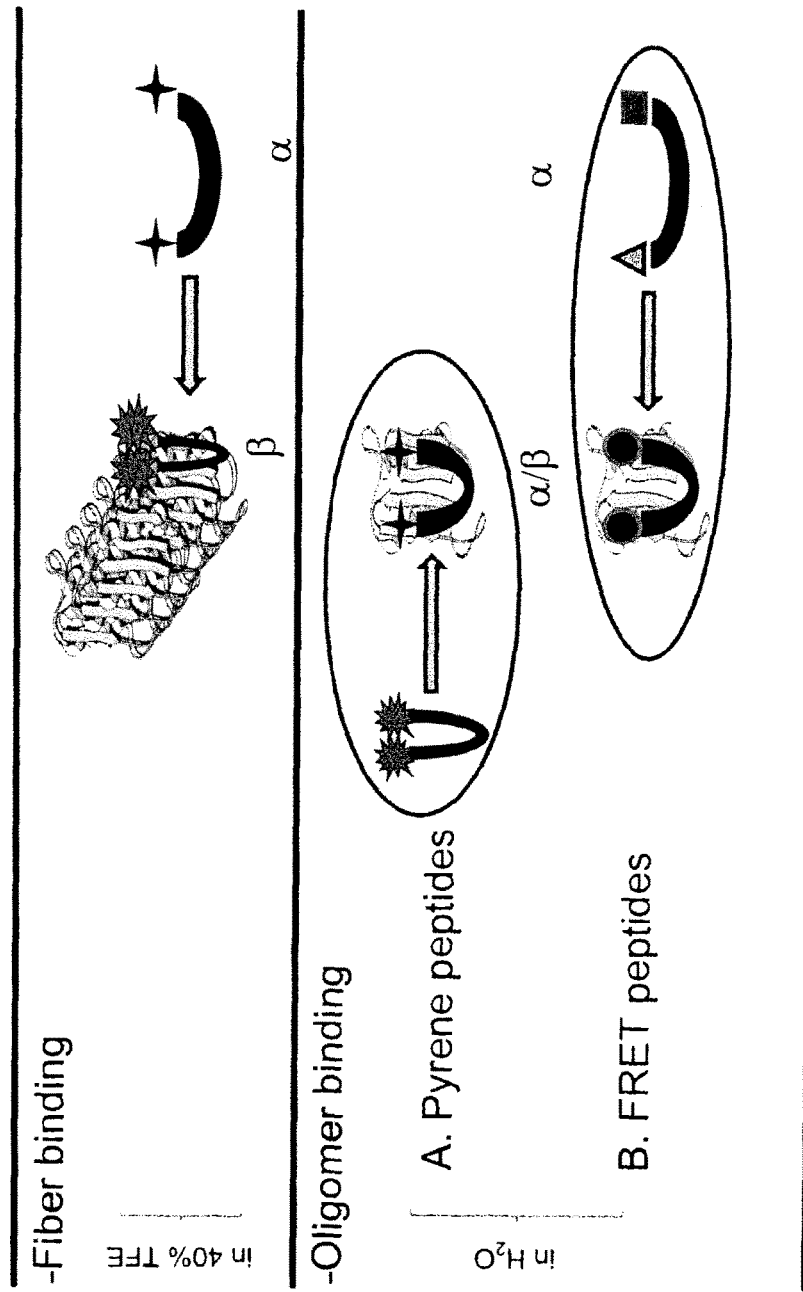
FIG. 10 illustrates conformational changes of peptide probes described herein upon binding to different substrates. Top panel: A peptide probe (such as SEQ ID NO:1) labeled with pyrene at each terminus adopts increased β-sheet conformation upon binding to Aβ fibers in 40% TFE, as detected by an increased pyrene excimer signal. Bottom panel A: A peptide probe (such as Peptide 22, SEQ ID NO:2) labeled with pyrene at each terminus adopts a less ordered (e.g., decreased β-sheet) conformation upon binding to Aβ oligomers in water, as detected by an increased pyrene monomer ("self") signal. Bottom panel B: A peptide probe labeled with FRET labels at each terminus adopts an increased β-sheet conformation upon binding to Aβ oligomers in water, as detected by the FRET signal. Peptide probes AD293 (SEQ ID NO:52), AD292 (SE ID NO:53), AD 291 (SEQ ID NO:54) and AD 290 (SEQ ID NO:55) have exhibited fluorescence behavior consistent with this type of conformation change.

FIG. 10 schematically illustrates several different embodiments of the methods and probes described herein.

(i) Aβ Fiber Assay (Top Panel)

An Aβ fiber assay may be conducted in an organic solvent, such as 40% TFE. As illustrated in the top panel of FIG. 10, peptide probe (e.g., SEQ ID NO:1) labeled at each terminus with pyrene incubated in 40% TFE in the absence of Aβ fibers exhibits a conformation that is primarily alpha helical, as can be observed by CD spectroscopy (data not shown). This conformation is associated with the monomer or self fluorescence of the pyrene moieties (370-410 nm; see FIG. 6). Upon introduction of an Aβ fiber substrate, the probe adopts a β-sheet conformation. This conformation is associated with the excimer fluorescence of the pyrene moieties (430-530 nm; see FIG. 6).

(ii) Aβ Oligomer Assay (Bottom Panel)

An Aβ oligomer assay may be conducted in an aqueous solvent, such as water. As illustrated in bottom panel A of FIG. 10, peptide probe 22 (e.g., SEQ ID NO:2) labeled at each terminus with pyrene in the absence of Aβ oligomer exhibits a conformation that associated with the excimer fluorescence of the pyrene moieties (see FIG. 11), and so is believed to have an increased β-sheet structure. Upon introduction of Aβ oligomer, the fluorescence profile shifts to primarily self-fluorescence (monomeric) (see FIG. 11), which is associated with reduced β-sheet structure, or increased alpha helix structure.

Alternatively, as illustrated in bottom panel B of FIG. 10, a peptide probe can be labeled at each terminus with members of a FRET pair (e.g. FAM and EDANS). In accordance with the illustrated embodiments, the FRET labels do not interact in the absence Aβ oligomer, whereas upon introduction of Aβ oligomer, the fluorescence profile shifts to FRET-fluorescence, which is associated with increased β-sheet structure. Peptide probes AD293 (SEQ ID NO:52), AD292 (SE ID NO:53), AD 291 (SEQ ID NO:54) and AD 290 (SEQ ID NO:55) have exhibited fluorescence behavior consistent with this type of conformation change.

The observations related to FIG. 10, bottom panel, suggest that, at least for these peptides, the nature of the labels may influence the folding properties and/or conformation of the peptide probes, in addition to the amino acid sequence of the peptide probes. Thus, pyrene labels may favor the formation of β-sheet structures that result in excimeric fluorescence in the absence of Aβ oligomer. On the other hand, FRET pairs do not seem to interact as strongly in the absence of substrate.

Example 7

As discussed above, Peptide 22 (SEQ ID NO: 2) undergoes a conformational change upon interaction with Aβ oligomer. FIG. 11 illustrates the fluorescence spectra for Peptide 22 labeled at each terminus with pyrene and incubated in aqueous conditions for several hours at room temperature in 10 mM Hepes (pH 7.0). The fluorescence of Peptide 22 is stable over time in the absence of oligomer (no increase in monomer or excimer flourescence), but exhibits an increase in pyrene monomer signal when incubated with soluble Aβ oligomers. (solid line=Time 0; dashed line=3 hours; dotted line=18 hours). Specifically, and as shown in FIG. 11 (right panel), Peptide 22 exhibits a time-dependent conformation shift from pyrene excimeric (emission maxima at ~460 and 485 nm) to pyrene monomeric (emission maxima at ~380 and 400 nm).

Example 8

This example illustrates the specificity of Peptide 22 for Aβ oligomers.

Peptide 22 (100 nM) is incubated in water for 15 hours at room temperature with equimolar concentrations (0, 30, 100, and 300 nN) of several potential Aβ substrates: Aβ42 oligomer (type 1); Aβ42 oligomer (type 2); Aβ1-42 monomer; Aβ1-40 monomer; Aβ1-42 fiber; Aβ1-40 fiber; bovine serum albumin (control substrate); and carbonic anhydrase (control substrate).

As show in FIG. 12, Peptide 22 exhibits a dose-dependent fluorescence response with regard to the two Aβ oligomer substrates, characterized by an increase in pyrene monomeric (self) fluorescence with increased oligomer load. Aβ42 monomer and Aβ40 fiber induced a slight fluorescence response at the high substrate load. These data demonstrate that under aqueous condition, the Peptide 22 fluorescence response is target-specific and dose-responsive.

Example 9

This example further studies the reacitivity of Peptide 22.

Figure 13:
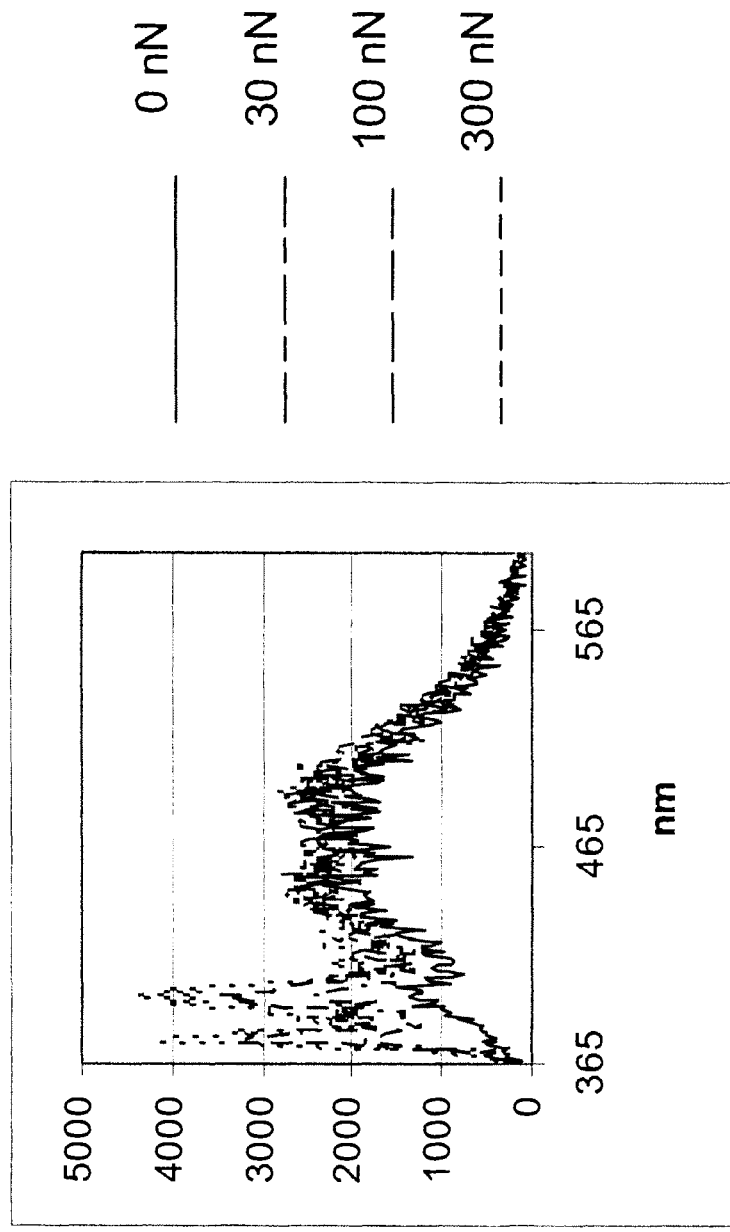
Figure 13:
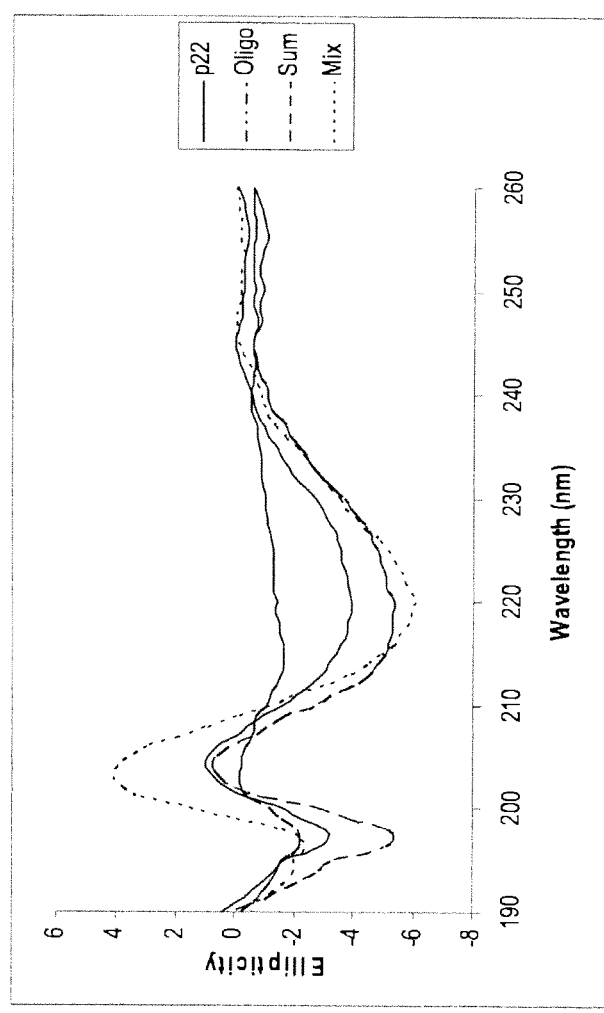

With reference to FIG. 13A, Peptide 22 (70 nM) is incubated with 0, 30, 100, or 300 nN synthetic Aβ42 oligomer at 25 C, and fluorescence emission spectra is recorded after 3 hours incubation. As shown in FIG. 13 (top panel), in the absence of Aβ42 oligomer, Peptide 22 displays very little pyrene monomer (self) fluorescence (370-420 nm). However, pyrene monomer (self) fluorescence increases with Aβ42 oligomer concentration in a dose-dependent manner. For example, and as shown in FIG. 13, Peptide 22 shows greater pyrene monomer fluorescence when incubated with 300 nN Aβ42 oligomer than with 30 Aβ42 oligomer. (solid line—no Aβ42 oligomer; dashed/dot line—30 nN Aβ42 oligomer; large dashed line—100 nN Aβ42 oligomer; small dashed line—300 nN Aβ42 oligomer)

Circular dichroism (CD) analysis is used to determine the secondary structure of Peptide 22, synthetic Aβ42 oligomer, and a mixture thereof. Samples are incubated in 10 mM sodium phosphate (pH 7.0) for 3 hours at room temperature before measuring CD. For each sample, the relative ellipticity is evaluated from 190-260 nm. FIG. 13 (bottom panel) shows CD profiles of 4 μM Peptide 22 (solid line); 33 nM synthetic Aβ42 oligomer (dashed/dot line); the arithmetical sum of the two individual samples (large dashed line); a mixture of Peptide 22 and synthetic Aβ42 oligomer mixture (small dashed line). Each data set represents the average of three separate spectral scans.

The data show that Peptide 22 alone has a primarily β sheet secondary structure (36%), whereas the synthetic Aβ42 oligomer is essentially unstructured (i.e., ellipticity is zero). When the two species are incubated together, the structure of Peptide 22 remains primarily β sheet (43%), with a profile that is very similar to the sum of the two individual components.

The data suggest that the conformational change that occurs upon interaction of Peptide 22 with Aβ42 oligomer that alters the fluorescence profile of Peptide 22 is not detectable by CD, and so does not significantly alter the overall β-sheet content of the peptide or peptide-oligomer complexes.

Example 10

Exemplary peptide probes designed in accordance with the principles described above are set forth in Table 1 below. As shown by shading in the sequences, most of the peptide sequences are based on amino acids 16-35 of the Aβ peptide (WT; SEQ ID NO:1), which is a β-sheet forming region of the Aβ peptide (others are based on longer portions of the Aβ peptide), with an added C-terminal lysine residue to facilitate labelling. The category (or categories) of the sequence variants are indicated in the table (e.g., modified to improve stability, provide a salt bridge, increase solubility, faciliatate alpha-helix formation, destabilize β-sheet structure, add an Aβ binding motif, etc.). Also illustrated are options for peptide probe labeling, including different label sites and label pairs. Unless indicated otherwise, all peptides were labeled with two pyrene labels, one on the N-terminal amine, and the other on a side chain of a C-terminal lysine residue. Additionally, unless indicated otherwise, all constructs contain a C-terminal amide in place of the carboxyl group.

The following abbreviations are used in the table:
"PBA"=pyrene butyric acid
"r"=d-Arginine
"Dabcyl"=4-(4-dimethylaminophenyl) diazenylbenzoic acid
"EDANS"=5-(2'-aminoethyl)aminonaphthalene-1-sulfonic acid
"FAM"=5(6)carboxyfluorescein
"Dansyl"=5-dimethylaminonaphthalene-1-sulfonyl

TABLE 1

| | | | | |
|---|---|---|---|---|
| | | Peptide Probes | | |
| SEQ ID NO: | Category | Name | Modification | Sequence |
| 1 | Wildtype | WT | Aβ protein residues 16-35, with added C-Terminal Lys | KLVFF AEDVG SNKGA IIGLM K |

TABLE 1-continued

Peptide Probes

| SEQ ID NO: | Category | Name | Modification | Sequence |
|---|---|---|---|---|
| 6 | Stability | AD250 | M35A to replace oxidizable methionine residue | KLVFF AEDVG SNKGA IIGLA K |
| 2 | Salt Bridge | P22 | Salt bridge at G29H and G33E, also induce alpha-helix, and increase solubility | KLVFF AEDVG SNKHA IIELM K |
| 14 | | P22 v.1 | Salt bridge at G29R and G33E | KLVFF AEDVG SNKRA IIELM K |
| 15 | | P22 v.2 | Salt bridge at G29K and G33E | KLVFF AEDVG SNKKA IIELM K |
| 3 | Salt Bridge + Alpha Helix | P38 | Salt bridge at G29H and G33E; Ala substitutions to increase alpha-helicity | KLVFF AEDAA AAKHA IIELM K |
| 4 | | P45 | Salt bridge at G29H and G33E; Ala additions to increase alpha-helicity | KAAA KLVFF AEDVG SNKHA IIELM K |
| 16 | Salt Bridge + Aβ Binding Motif | P77 | Salt bridge; Additional Aβ binding motif (GxxEG; SEQ ID NO: 25); extended N-terminus | HHQ KLVFF AEDEG SRKHA IE<u>GLM EG</u> K |
| 17 | | P59 | Salt bridge; Additional Aβ binding motif (GxxEG; SEQ ID NO: 25) | EAA KLVFF AEDEG SRKHA IE<u>GLM EG</u> K |
| 19 | Based on Naturally Occurring Mutants | Italian | P22, with E22K point mutation | KLVFF AKDVG SNKHA IIELM K |
| 20 | | Dutch | P22, with E22Q point mutation | KLVFF AQDVG SNKHA IIELM K |
| 21 | | Arctic | P22, with E22G point mutation | KLVFF AGDVG SNKHA IIELM K |
| 22 | Solubility | AD272 | WT, with 2 C-terminal dArg residues, and alternalte label site | (PBA)KLVFF AEDVG SNKGA IIGLM K(PBA)rr |
| 23 | | AD316 | P22, with 2 C-terminal dArg residues, and alternalte label site | PBA-KLVFF AEDVG SNKHA IIELM K(PBA)rr |
| 24 | | AD305 | P22, with 2 N-terminal dArg residues, 2 C-terminal E residues and alternalte label site | rrK(PBA)LVFF AEDVG SNKHA IIELM K(PBA)EE |
| 1 | | AD274 | WT, with PEG10 at C-terminus | (PBA)KLVFF AEDVG SNKGA IIGLM K(PBA)PEG10 |
| 26 | | AD271 | P45, with two dArg residues at C-terminus | (PBA)KAAA KLVFF AEDVG SNKHA IIELM K(PBA)rr |
| 27 | Induce Alpha-Helix + Solubility | AD273 | WT, with addition of Ala stretch (for alpha-helix formation) and dArg residues (for solubility) | (PBA)KAAA KLVFF AEDVG SNKGA IIGLM K(PBA)rr |
| 28 | Reduce Stability of B-sheet | AD323 | P22, with point mutations H29D and I31D | KLVFF AEDVG SNKDA DIELM K |

TABLE 1-continued

Peptide Probes

| SEQ ID NO: | Category | Name | Modification | Sequence |
|---|---|---|---|---|
| 29 | | AD325 | P22, with point mutation S26D | KLVFF AEDVG DNKHA IIELM K |
| 30 | | AD330 | P22, with point mutation I31D | KLVFF AEDVG SNKHA DIELM K |
| 31 | | AD329 | P22, with point mutation L34D | KLVFF AEDVG SNKHA IIEDM K |
| 32 | | AD328 | P22, with point mutation H29D | KLVFF AEDVG SNKDA IIELM K |
| 33 | | AD327 | P22, with point mutation S26D, I31D | KLVFF AEDVG DNKHA DIELM K |
| 34 | | GM6 | P22, with point mutations F19S, L34P | KLVSF AEDVG SNKHA IIEPM K |
| 35 | | GM6 var.1 | P22, with point mutation F19S | KLVSF AEDVG SNKHA IIELM K |
| 5, 18 | | I32S | Wildtype, with I32S point mutation | KLVFF AEDVG SNKGA ISGLM K |
| 36 | Label (PBA) Site | AD266 | WT, with label on side chain of N-terminal Lys | K(PBA)LVFF AEDVG SNKGA IIGLM K(PBA) |
| 37 | | AD268 | WT, with label on side chain of near N-terminal Lys; addition of solubilizing dArg and E residues | EK(PBA)LVFF AEDVG SNKGA IIGLM K(PBA)rrr |
| 38 | Biotin | AD310 | P22, biotin labeled with helical linker at C-terminus | (PBA)KLVFF AEDVG SNKHA IIELM K(PBA)EAAAK(biotin) |
| 39 | | AD313 | P22, biotin labeled at side chain of internal Lys | (PBA)KLVFF AEDVG SNK(biotin)HA IIELM K(PBA) |
| 40 | | AD314 | P22, biotin labeled with flexible linker at C-terminus | (PBA)KLVFF AEDVG SNKHA IIELM K(PBA)GSSGSSK(biotin) |
| 41 | | AD317 | P22, biotin labeled with thrombin site linker, at C-terminus | (PBA)KLVFF AEDVG SNKHA IIELM K(PBA)GLVP RGSGK(biotin) |
| 42 | | AD321 | P22, biotin labeled with "kinked" linker at C-terminus | (PBA)KLVFF AEDVG SNKHA IIELM K(PBA)PSGSPK(biotin) |
| 2, 43 | Label/Quencher Pairs | AD326 | P22, with pyrene and Dabcyl quencher | (PBA)KLVFF AEDVG SNKHA IIELM K(Dabcyl) |
| 44 | | AD309 | WT, with EDANS and Dabcyl quencher and solubilizing E residue | E(EDANS)LVFF AEDVG SNKGA IIGLM K(Dabcyl) |
| 45 | | AD306 | Wildtype Aβ residues 5-42, with EDANS and Dabcyl quencher and solubilizing E residue | E(EDANS)R HDSGY EVHHQ KLVFF AEDVG SNKGA IIGLM VGGVV IA K(Dabcyl) |
| 46 | | AD303 | Wildtype Aβ residues 3-35, with EDANS and Dabcyl quencher and solubilizing E residue | E(EDANS)EFR HDSGY EVHHQ KLVFF AEDVG SNKGA IIGLM K(Dabcyl) |
| 47 | | AD302 | P59, with EDANS and Dabcyl quencher and solubilizing E residue | E(EDANS)AAA KLVFF AEDEG SRKHA IEGLM EGK(Dabcyl) |

TABLE 1-continued

Peptide Probes

| SEQ ID NO: | Category | Name | Modification | Sequence |
|---|---|---|---|---|
| 48 | | AD301 | P77, with EDANS and Dabcyl quencher and solubilizing E residue | E(EDANS)HHQ KLVFF AEDEG SRKHA IEGLM EGK(Dabcyl) |
| 49 | | AD300 | P22 with EDANS and Dabcyl quencher and solubilizing E residue | E(EDANS)LVFF AEDVG SNKHA IIELM K(Dabcyl) |
| 50 | FRET Pairs | AD295 | P22, with Dansyl and Trp | (Dansyl)KLVFF AEDVG SNKHA IIELM W |
| 51 | | AD294 | WT, with FAM and EDANS and solubilizing E residue | (FAM)KLVFF AEDVG SNKGA IIGLM E(EDANS) |
| 52 | | AD293 | P22,with FAM and EDANS and solubilizing E residue | (FAM)KLVFF AEDVG SNKBA IIELM E(EDANS) |
| 53 | | AD292 | Aβ residues 3-35, with FAM and EDANS and solubilizing E residue | (FAM)EFR HDSGY EVHHQ KLVFF AEDVG SNKGA IIGLM E(EDANS) |
| 54 | | AD291 | P77, with FAM and EDANS and solubilizing E residue | (FAM)HHQ KLVFF AEDEG SRKHA IEGLM EGE(EDANS) |
| 55 | | AD290 | P59, with FAM and EDANS, additional Ala, and solubilizing E residue | (FAM)EAA KLVFF AEDEG SRKHA IEGLM EGE(EDANS) |

The peptides based on naturally-occurring mutants are expected to have an enhanced ability to form aggregate species.

Peptide probes Peptide 22 (SEQ ID NO:2), Peptide 22 variation 1 (SEQ ID NO:14), Peptide 22 variation 2 (SEQ ID NO:15), Peptide 38 (SEQ ID NO:3) and Peptide 45 (SEQ ID NO:4) have been shown to react with Aβ42 oligomers in an aqueous assay. Surprisingly, this reactivity was characterized by a transition from primarily pyrene excimer fluorescence to pyrene self-fluorescence. The data suggest that these peptide probes undergo a conformational shift from a (β-sheet conformation to a reduced β-sheet or increased alpha helix conformation (or other conformation) upon interaction with Aβ42 oligomer under aqueous conditions.

To follow up on the P22 design, P22 variants having less stable β-sheet structures were created, with the expectation that the conformational transition observed upon interaction with Aβ42 oligomer would be more thermodynamically favored than observed with the P22 sequence. These peptides have been synthesized and are listed in Table 1 above.

As indicated in Table 1, peptides were constructed with FRET pairs or with Dabcyl quencher moieties that quench the fluorescence signaling of the paired fluorescence moiety (e.g, EDANS). These peptides with alternative label pairs may allow for greater sensitivity in aqueous assays.

When a peptide probe that undergoes a conformational shift from a β-sheet conformation to a reduced β-sheet or increased alpha helix conformation (or other conformation) upon interaction with Aβ42 oligomer (such as Peptide 22) is labeled with a fluorescent label/quencher pair as illustrated in Table 1 above, the fluorescent label signal initially is quenched, and then is unquenched when the peptide probe undergoes the conformational shift upon interaction with Aβ42 oligomer, resulting in induction of the fluorescent signal.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with the true scope and spirit of the invention being indicated by the following claims.

What is claimed is:

1. A peptide probe for Aβ protein, wherein the peptide probe is a peptide or peptide mimic that comprises an amino acid sequence that
   (i) is a variant of SEQ ID NO: 1 that differs from SEQ ID NO: 1 by one or more amino acid substitutions selected from G29H, G29R, G29K, and G33E that introduces a salt bridge into the peptide probe sequence wherein G29H, G29R and G29K correspond to residue 14 of SEQ ID NO:1 and G33E corresponds to residue 18 of SEQ ID NO:1; or
   (ii) comprises the amino acid sequence selected from SEQ ID NOs: 2-4, 14-17, 19-21, 23-24, 28-35, 38-43, 49-50 and 52, having a salt bridge in the peptide probe sequence.

2. The peptide probe of claim 1, wherein the peptide probe is labeled with a detectable label.

3. The peptide probe of claim 2, wherein the peptide probe is labeled with two or more labels.

4. The peptide probe of claim 3, wherein the peptide probe is labeled with a detectable label pair selected from an excimer pair, a FRET pair and a fluorophore/quencher pair.

5. The peptide probe of claim of claim 1, wherein the amino acid sequence of the peptide probe is a variant of SEQ ID NO: 1 that differs from SEQ ID NO: 1 by one or more substitutions selected from the group consisting of G29H, G29R, G29K, and G33E.

6. The peptide probe of claim 1, wherein the amino acid sequence of the peptide probe comprises the amino acid sequence selected from the group consisting of SEQ ID NOs: 2-4, 14-17, 19-21, 23-24, 28-35, 38-43, 49-50 and 52.

7. The peptide probe of claim 1, wherein the amino acid sequence of the peptide probe comprises the amino acid sequence of SEQ ID NO: 2 (Peptide 22).

8. The peptide probe of claim 1, wherein the peptide probe is conjugated to a soluble polyethylene glycol moiety.

9. The peptide probe of claim 2, wherein the detectable label is conjugated at a site selected from the group consisting of (i) a side chain of a terminal lysine residue; (ii) a side chain of an internal lysine residue.

10. The peptide probe of claim 1, wherein the peptide probe is conjugated to a biotin moiety directly or through a peptide linker.

11. The peptide probe of claim 10, wherein the linker comprises an amino acid sequence selected from the group consisting of SEQ ID NOs: 56-60.

12. The peptide probe of claim 10, wherein the peptide probe is conjugated to a biotin moiety through a side chain of an internal lysine residue.

* * * * *